US010632202B2

(12) United States Patent
Bai et al.

(10) Patent No.: US 10,632,202 B2
(45) Date of Patent: Apr. 28, 2020

(54) PRESERVATIVE CONTAINING COMPOSITIONS

(71) Applicant: JOHNSON & JOHNSON CONSUMER INC., Skillman, NJ (US)

(72) Inventors: Mingqi Bai, Morris Plains, NJ (US); Kenneth T. Holeva, Phillipsburg, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 15/442,152

(22) Filed: Feb. 24, 2017

(65) Prior Publication Data

US 2017/0252451 A1 Sep. 7, 2017

Related U.S. Application Data

(60) Provisional application No. 62/303,939, filed on Mar. 4, 2016.

(51) Int. Cl.

| | |
|---|---|
| A61K 31/14 | (2006.01) |
| A01N 33/12 | (2006.01) |
| A61K 47/38 | (2006.01) |
| A01N 59/14 | (2006.01) |
| A01N 43/50 | (2006.01) |
| A01N 43/08 | (2006.01) |
| A01N 43/16 | (2006.01) |
| A61K 31/19 | (2006.01) |
| A01N 31/02 | (2006.01) |
| A01N 37/44 | (2006.01) |
| A61K 33/22 | (2006.01) |
| A01N 37/36 | (2006.01) |
| A61K 33/14 | (2006.01) |
| A61K 31/728 | (2006.01) |
| A61K 9/08 | (2006.01) |
| A61K 9/00 | (2006.01) |
| A61K 31/4164 | (2006.01) |
| A61K 31/4402 | (2006.01) |
| A61K 47/02 | (2006.01) |
| A61K 47/10 | (2017.01) |
| A61K 47/12 | (2006.01) |
| A61K 47/18 | (2017.01) |
| A61K 47/22 | (2006.01) |
| A61K 47/26 | (2006.01) |

(52) U.S. Cl.
CPC ............. *A61K 47/38* (2013.01); *A01N 31/02* (2013.01); *A01N 33/12* (2013.01); *A01N 37/36* (2013.01); *A01N 37/44* (2013.01); *A01N 43/08* (2013.01); *A01N 43/16* (2013.01); *A01N 43/50* (2013.01); *A01N 59/14* (2013.01); *A61K 9/0048* (2013.01); *A61K 9/08* (2013.01); *A61K 31/14* (2013.01); *A61K 31/19* (2013.01); *A61K 31/4164* (2013.01); *A61K 31/4402* (2013.01); *A61K 31/728* (2013.01); *A61K 33/14* (2013.01); *A61K 33/22* (2013.01); *A61K 47/02* (2013.01); *A61K 47/10* (2013.01); *A61K 47/12* (2013.01); *A61K 47/186* (2013.01); *A61K 47/22* (2013.01); *A61K 47/26* (2013.01)

(58) Field of Classification Search
CPC ....... A61K 31/14; A61K 9/0048; A01N 33/12
See application file for complete search history.

(56) References Cited

U.S. PATENT DOCUMENTS

| | | | |
|---|---|---|---|
| 7,550,418 B2 * | 6/2009 | Tsao ..................... | A61L 12/08 510/112 |
| 2002/0123482 A1 | 9/2002 | Chowhan et al. | |
| 2008/0138310 A1 | 6/2008 | Ketelson et al. | |
| 2011/0319502 A1 * | 12/2011 | Coffey ................. | A61K 9/0048 514/777 |
| 2012/0070401 A1 | 3/2012 | Zhang et al. | |
| 2014/0221309 A1 | 8/2014 | Beard et al. | |

FOREIGN PATENT DOCUMENTS

| | | |
|---|---|---|
| WO | WO 96/14829 | 5/1996 |
| WO | WO 98/32421 | 7/1998 |
| WO | 2002024116 A1 | 3/2002 |
| WO | WO 02/38161 A1 | 5/2002 |
| WO | WO 02/49615 A2 | 6/2002 |
| WO | WO 02/049615 A3 | 6/2002 |
| WO | WO 2008/036847 A3 | 3/2008 |
| WO | WO 2009/117242 A3 | 9/2009 |
| WO | WO-2009117242 A2 * | 9/2009 ........... A61K 9/0048 |
| WO | WO 2011/162951 A1 | 12/2011 |
| WO | WO 2013/166399 A1 | 11/2013 |
| WO | WO 2013/169458 A1 | 11/2013 |
| WO | WO-2013169458 A1 * | 11/2013 ........... A61K 9/0048 |

OTHER PUBLICATIONS www.Drugs.com, Vlsine Tired Eye Dry Eye Relief, Johnson & Johnson Consumer Inc, marketed Feb. 5, 2016, pp. 1-5. (Year: 2016).*
European Pharmacopoeia 8.0 (European Pharmacopoeia 8.0, 5.1.3. Efficacy of Antimicrobial Preservation).
Clinical Ophthalmology, Dovepress, Torkildsen, G., et al.; Safety and comfort evaluation of a new formulation of Visine® lubricant eye drops containing HydroBlend™ and GentlePur™, 2016:10; pp. 331-336.
International Search Report dated May 4, 2017—PCT/US2017/020305.

* cited by examiner

*Primary Examiner* — Craig D Ricci
*Assistant Examiner* — Janet L. Coppins

(57) ABSTRACT

The present invention relates to compositions providing improved preservative efficacy. The present invention further relates to polyquaternium compound containing compositions having improved the antifungal activity. In certain embodiments, the present invention relates to ophthalmic compositions comprising a polyquaternium compound, a polyol or combination of polyols, borate compound, and an antimicrobial mixture comprising electrolytes and nutrients.

4 Claims, No Drawings

PRESERVATIVE CONTAINING COMPOSITIONS

CROSS-REFERENCE TO RELATED APPLICATION

The present application claims the benefit of the earlier filing date of U.S. provisional patent application 62/303,939, filed Mar. 4, 2016, the entirety of which application is hereby incorporated by reference herein as if fully set forth herein.

FIELD OF THE INVENTION

The present invention relates to compositions providing improved preservative efficacy. The present invention further relates to polyquaternium compound containing compositions having improved the antifungal activity. In certain embodiments, the present invention relates to ophthalmic compositions comprising a polyquaternium compound, a polyol or combination of polyols, borate compound, and an antimicrobial mixture comprising electrolytes and nutrients.

BACKGROUND OF THE INVENTION

Ophthalmic solutions are sterile solutions, free or substantially free from foreign particles and/or microorganisms, for instillation into the eye. For certain applications, ophthalmic solutions do not contain medications and are only used as lubricating, tear-replacing, and/or eye wash solutions. Ophthalmic solutions can also contain pharmacologically active ingredients and be used to treat such environment related eye conditions as dry eye, allergies, eye infections such as pink eye, minor eye irritations or conjunctivitis, or structurally related eye conditions such as glaucoma. They can also be used diagnostically by opticians as mydriatic compositions to dilate the pupils of patients during eye examinations.

To avoid introducing infective agents into the eye, it is critical that ophthalmic solutions have and maintain antimicrobial properties by adequately preserving such solutions in their storage containers between uses. Polyquaternium compounds are polycationic polymers that are used as surfactants in the personal care industry. Some have antimicrobial properties, and are useful as preservatives in ophthalmic and/or contact lens solutions.

An issue with the polyquaternium compounds, including the specific compound polyquaternium-42, is their limited ability to provide robust antifungal effectiveness. There is, therefore, a need for compositions useful as ophthalmic solutions having improved antifungal effectiveness, particularly toward the mold *Aspergillus brasiliensis*.

SUMMARY OF THE INVENTION

The present inventors have found that compositions having improved antifungal activity and overall preservative efficacy can be obtained by combining: i) polyquaternium compounds, ii) optionally, polyols, iii) borates and iv) an antimicrobial mixture comprising electrolytes and nutrients as described in further detail below.

The present inventors have further found that polyquaternium compound containing compositions having improved antifungal activity can be obtained by combining: i) polyquaternium compounds and a saccharide selected from monosaccharides, disaccharides, isomers thereof and mixtures thereof as described in further detail below.

The compositions of the present invention satisfy the acceptance criteria of the EP B Criteria (defined below), exhibiting a log reduction in fungal micro-organisms selected from the group consisting of *Candida albicans*, *Aspergillus brasiliensis* and mixtures thereof of greater than or equal to 1 log reduction after 14 days when tested in accordance with the EP B Criteria, or optionally a log reduction of greater than or equal to 2 (or about 2) log reductions after 14 days when tested in accordance with the EP B Criteria.

The present invention relates to compositions, comprising:
a) from about 0.0005% w/v (weight to volume) to about 0.1000% w/v, of the total composition, of a polyquaternium compound;
b) optionally, from about 0.2% w/v to about 2.0% w/v, of the total composition, of an amount of a polyol or combination polyols;
c) from about 0.02% w/v to about 1.5% w/v, of the total composition, of a borate; and
c) an antimicrobial mixture comprising:
  i. one or more nutrients; and
  ii. optionally, one or more electrolytes
such that:
  a. the total nutrient concentration, in the total composition, is from about 1.0 mMol/L to about 4.0 mMol/L of the composition; and
  b. when present, the total electrolyte concentration, in the total composition, is from about 20.0 mMol/L to about 80.0 mMol/L of the composition.

The present invention further relate to the use of such compositions for treating or preventing such eye conditions as dry eye, eye allergy (such as caused by plant spores [e.g., pollen or rag weed]), and minor eye irritations such as caused by chlorinated water, dust or smoke particles.

The present invention further relates to compositions comprising the following formulation:
a. from about 0.01% w/v (weight to volume) to about 0.2% w/v vasoconstictor;
b. from about 0.0015% w/v to about 0.0036% w/v polyquaternium 42;
c. from about 0.2% w/v to about 1.2% w/v polyethylene glycol 400;
d. from about 0.2% w/v to about 1.3% w/v glycerin;
e. from about 0.004% w/v to about 0.6% w/v borate;
f. from about 0.05% w/v to about 0.2% w/v lactate or pharmaceutically acceptable salt thereof;
g. from about 0.003% w/v to about 0.4% w/v, optionally 0.003% to about 0.04% w/v glucose;
h. from about 0% w/v to about 2.5% w/v hypromellose; and
i. water.

The present invention further relates to compositions, comprising:
a) from about 0.0005% w/v (weight to volume) to about 0.1000% w/v, of the total composition, of a polyquaternium compound; and
b) from about 0.002% w/v to about 1% w/v, of saccharide selected from monosaccharide, disaccharide, isomers thereof or mixtures thereof.

The present invention further relates a method for preventing the growth of viable (or live) fungal organisms, or reducing the number of viable fungal organisms (such as molds [e.g., *Aspergillus brasiliensis*]) in an environment or medium (such as a culture medium; a composition; or the closed or open environment of a container containing a composition where the container is, respectively, closed or open), comprising the steps of;
  a.) preparing a composition comprising:
    i) from about 0.0005% w/v (weight to volume) to about 0.1000% w/v, of the total composition, of a polyquaternium compound; and
    ii) from about 0.002% w/v to about 1% w/v, of saccharide selected from monosaccharide, disaccharide, isomers thereof or mixtures thereof; and
  b.) administering (or adding) the composition to the environment or medium.

The present invention further relates to methods for improving the overall preservative efficacy of a liquid composition, comprising the step of combining:
  a) from about 0.0005% w/v (weight to volume) to about 0.1000% w/v, of the total composition, of a polyquaternium compound;
  b) optionally, from about 0.2% w/v to about 2.0% w/v, of the total composition, of an amount of a polyol or combination polyols;
  c) from about 0.02% w/v to about 1.5% w/v, of the total composition, of a borate; and
  d) an antimicrobial mixture comprising:
    i. one or more nutrients; and
    ii. optionally, one or more electrolytes
  such that:
    a. the total nutrient concentration, in the total composition, is from about 1.0 mMol/L to about 4.0 mMol/L of the composition; and
    b. when present, the total electrolyte concentration, in the total composition, is from about 20.0 mMol/L to about 80.0 mMol/L of the composition.

The present invention still further relates to methods for improving the antifungal activity of a liquid composition, comprising the step of combining:
  a) from about 0.0005% w/v (weight to volume) to about 0.1000% w/v, of the total composition, of a polyquaternium compound;
  b) optionally, from about 0.2% w/v to about 2.0% w/v, of the total composition, of an amount of a polyol or combination polyols;
  c) from about 0.02% w/v to about 1.5% w/v, of the total composition, of a borate; and
  d) an antimicrobial mixture comprising:
    i. one or more nutrients; and
    ii. optionally, one or more electrolytes
  such that:
    a. the total nutrient concentration, in the total composition, is from about 1.0 mMol/L to about 4.0 mMol/L of the composition; and
    b. when present, the total electrolyte concentration, in the total composition, is from about 20.0 mMol/L to about 80.0 mMol/L of the composition.

DETAILED DESCRIPTION OF THE INVENTION

As indicated above, the present invention relates to compositions comprising a polyquaternium compound such as polyquaternium-42, a polyol compound (or mixture of polyols), a borate compound and an antimicrobial mixture.

The compositions and methods of the present invention can comprise, consist of, or consist essentially of the steps, essential elements and limitations of the invention described herein, as well any of the additional or optional ingredients, components, or limitations described herein. The term "comprising" (and its grammatical variations) as used herein is used in the inclusive sense of "having" or "including" and not in the exclusive sense of "consisting only of." The terms "a" and "the" as used herein are understood to encompass the plural as well as the singular.

Unless otherwise indicated, all documents cited are, in relevant part, incorporated herein by reference; the citation of any document is not to be construed as an admission that it is prior art with response to the present invention. Furthermore, all documents incorporated herein by reference are only incorporated herein to the extent that they are not inconsistent with this specification.

In certain embodiments, the present invention as disclosed herein may be practiced in the absence of any compound or element (or group of compounds or elements) which is not specifically disclosed herein.

Polyquaternium Compound

The compositions of the present invention comprise a polyquaternium compound. Polyquaternium is the International Nomenclature for Cosmetic Ingredients designation for several polycationic polymers that are used in the personal care industry. These polymers have quaternary ammonium centers in the polymer. INCI has approved at least 37 different polymers under the polyquaternium designation. They are cationic molecules. Some have antimicrobial properties, and find particular application in conditioners, shampoo, hair mousse, hair spray, hair dye, and contact lens solutions. Different polymers are distinguished by the numerical value that follows the word "polyquaternium". The numbers are assigned in the order in which they are registered rather than because of their chemical structure. Some of the more common quaternary ammonium compounds include those generically referred to in the art as polyquaternium.

In some embodiments, the composition will contain one or more of a polyquaternium compound(s) having a weight average molecular weight of from about 150 to about 15,000 Daltons, optionally from about 200 to about 13,500 Daltons, or optionally from about 250 to about 12,000 Daltons at a level of from about 0.0005% w/v to about 0.1000% w/v, or from about 0.0010% w/v to about 0.0200% w/v, or from about 0.0010% w/v to about 0.0050% w/v of the total composition.

Examples of suitable polyquaternium compounds include, but are not limited to, polyquaternium-1, polyquaternium-10, polyquaternium-42 or mixtures. In an embodiment of the present invention, the polyquaternium compound is polyquaternium-42.

Polyquaternium-1 is also known as ethanol, 2,2',2"-nitrilotris-, polymer with 1,4-dichloro-2-butene and N,N,N', N'-tetramethyl-2-butene-1,4-diamine. Polyquaternium-10 is also known as quaternized hydroxyethyl cellulose. Polyquaternium-42 is also known as poly[oxyethylene(dimethylimino)ethylene (dimethylimino)ethylene dichloride].

Borate

The compositions of the present invention also comprise a borate. As used herein, the term "borate" shall refer to boric acid, salts of boric acid and other pharmaceutically acceptable borates, or combinations thereof. Suitable borates include, but are not limited to, boric acid; alkaline metal salts such as sodium borate, potassium borate; alkaline earth metal salts such as calcium borate, magnesium borate; transition metal salts such as manganese borate; and mixtures thereof.

The borate compound can be present in the composition of the present invention at concentrations of from about 0.004% w/v to about 1.5% w/v, optionally from about 0.01% w/v to about 1.2% w/v, or optionally from about 0.06% w/v to about 1.0% w/v of the total composition.

Antimicrobial Mixture

The compositions of the present invention also comprise an antimicrobial mixture comprising one or more nutrient(s) and, optionally, one or more electrolyte(s).

Nutrients useful in the antimicrobial mixture of the present invention include, but are not limited to, lactate salts (such as sodium lactate or potassium lactate), phosphate salts (such as sodium phosphate, disodium phosphate and potassium phosphate), monosaccharides (such as glucose, fructose or galactose), disaccharides, citrates (such as citric acid, sodium citrate, potassium citrate) and mixtures thereof.

In certain embodiments, the nutrients include (are selected from or selected from the group consisting of) lactate, glucose and mixtures thereof. The present inventors have observed that glucose provides a significant contribution to the antifungal activity of the antimicrobial mixtures. The lactate follows the glucose with regard to the significance of its contribution to the antifungal activity of the antimicrobial mixture. And, in certain embodiments, the lactate/glucose combination provides an even higher degree of the antifungal activity than glucose alone.

While it was observed that citrate, ascorbic acid or glycine, individually, contribute minimally to the antifungal activity of the antimicrobial mixture, it was found that the combination of citrate, ascorbic acid and glycine was observed to improve the antifungal contribution of each of the glucose or lactate to the antimicrobial mixture, with the largest improvement observed when the glucose and lactate are combined with citrate, ascorbic acid and glycine.

In certain embodiments, the antimicrobial mixture further comprises electrolytes useful in the antimicrobial mixture of the present invention include, but are not limited to, alkaline earth metal salts, such as alkaline earth metal inorganic salts, and mixtures thereof. Suitable examples include potassium salts such as potassium chloride and potassium phosphate), magnesium salts (such as magnesium chloride), sodium salts (such as sodium chloride); counter anions such as chloride and mixtures thereof.

In certain embodiments, the nutrient(s) and electrolyte(s) are present in the antimicrobial mixture such that when incorporated to form the compositions of the present invention: i) the total nutrient concentration, in the total composition of the present invention, is from about 1.0 mMol/L to about 4.0 mMol/L, optionally from about 2.0 mMol/L to about 3.0 mMol/L, or optionally from about 2.8 mMol/L to about 3.0 mMol/L of the composition; and, when incorporated, ii) the total electrolyte concentration, in the total composition of the present invention, is from about 20 mMol/L to about 80.0 mMol/L, optionally from about 30 mMol/L to about 70 mMol/L, or optionally from about 40 mMol/L to about 60 mMol/L of the composition In certain embodiments, one or more, optionally two or more, optionally three of more, optionally four or more of the nutrients and, optionally, one or more, optionally two or more, optionally three of more, optionally four or more of the electrolytes are present in the antimicrobial mixture such that:

A. the total nutrient concentration in the composition of the present invention comprises the individual nutrients in the following concentrations:

i) a lactate concentration of from about 0 mMol/L to about 10.0 mMol/L, optionally from about 1.0 mMol/L to about 6.0 mMol/L; or optionally 2.0 mMol/L to about 3.0 mMol/L of the total composition;
    ii) a citrate concentration of from about 0 mMol/L to about 0.5 mMol/L, optionally from about 0.01 mMol/L to about 0.10 mMol/L; or optionally 0.025 mMol/L to about 0.050 mMol/L of the total composition;
    iii) a phosphate concentration of from about 0 mMol/L to about 10 mMol/L, optionally from about 1 mMol/L to about 5 mMol/L; or optionally 1.5 mMol/L to about 2.5 mMol/L of the total composition;
    iv) a glucose concentration of from about 0.1 mMol/L to about 25 mMol/L, optionally from about 0.1 mMol/L to about 10 mMol/L; or optionally 0.1 mMol/L to about 0.4 mMol/L of the total composition;

and

B. optionally, the total electrolyte concentration in the total composition of the present invention comprises the individual electrolytes in the following concentrations:

i) a potassium concentration of from about 24 mMol/L to about 28 mMol/L of the total composition;
    ii) a sodium concentration of from about 5 mMol/L to about 10 mMol/L of the total composition;
    iii) a magnesium concentration of from about 0.50 mMol/L to about 0.80 mMol/L of the total composition;
    iv) a chloride concentration of from about 23 mMol/L to about 28 mMol/L of the total composition.

In certain embodiments, ascorbic acid is present at a concentration not exceeding 0.001% w/v, optionally at from about 0.00002% w/v to about 0.0001% w/v, or optionally from about 0.00001% w/v to about 0.00002% w/v, of the total composition.

In certain embodiments, the antimicrobial mixture is free of, or substantially free of, calcium, bicarbonate, low molecular weight amino acids and/or zinc ions. The term "substantially free" as used herein means a concentration less than 1% (or about 1%), optionally, less than 0.1% (or about 0.1%), optionally less than 0.01% (or about 0.01%), optionally less than 0.001% (or about 0.0.001%), or optionally less than 0.0001% (or about 0.0001%). Examples of low molecular weight amino acids include, but are not limited to, L-alanine, β-alanine, α-aminoadipic acid, α-aminobutyric acid, γ-aminobutyric acid, α-aminoisobutyric acid, arginine, asparagine, aspartic acid, citrulline, creatine, glutamic acid, glycine, histidine, cysteine, leucine, lysine, norleucine, ornithine, phenylalanine, phophoserine, sarcosine, threonine and valine.

In certain embodiments, glycine is present at a concentration not exceeding 0.0010% w/v, optionally at from about 0.00001% w/v to about 0.0002% w/v, or optionally from about 0.00002% w/v to about 0.0001% w/v, of the total composition.

The inventors further observed that mono- and di-saccharides such as glucose actually improve the antifungal activity of polyquaternium compounds such as polyquaternium 42. This is surprising as glucose agar medium is prescribed to preculture fungi for availability in preservative efficacy testing.

Monosaccharides suitable for use with the polyquaternium compounds either alone, or as part of the antimicrobial mixture include, but are not limited to (or, are selected from, or selected from the group consisting of), glucose, fructose, galactose, isomers thereof and mixtures thereof.

Disaccharides suitable for use with the polyquaternium compounds either alone or as part of the antimicrobial mixture include, but are not limited to (or, are selected from, or selected from the group consisting of), sucrose, lactulose, lactose, maltose, α,α-trehalose, β,β-trehalose, α,β-trehalose, cellobiose, chitobiose, kojibiose, nigerose, isomaltose, sophorose, laminaribiose, gentiobiose, turanose, maltulose, palatinose, gentiobiulose, mannobiose, melibiose, melibiulose, rutinose, rutinulose, xylobiose, isomers thereof and mixtures thereof.

In certain embodiments, the mono- and/or di-saccharides is present in compositions containing the polyquaternium compound at a concentration of from about 0.002% w/v to 1% (or about 1%) w/v, optionally at from about 0.002% w/v to about 0.8% w/v, or optionally at from about 0.003% w/v to about 0.4% w/v, of the total composition.

Polyol

In certain embodiments, the compositions of the present invention may further comprise a polyol or combination of polyols. In certain embodiments, the presence of additional components such as the pharmaceutically active compounds may require the addition of a polyol or combination of polyols. As used herein, and unless otherwise indicated, the term "polyol" shall refer to any compound having at least two —OH groups. The polyols can be linear or circular, substituted or unsubstituted, or mixtures thereof, so long as the resultant complex is water-soluble and pharmaceutically acceptable. Such polyol compounds include sugars, sugar alcohols, sugar acids, uronic acids and mixtures thereof. In certain embodiments, the polyols are sugars, sugar alcohols and sugar acids, including, but not limited to: mannitol, glycerin (glycerol), propylene glycol, polyethylene glycol, sorbitol and mixtures thereof. In certain embodiments, the polyols are polysorbate 80, mannitol, sorbitol, propylene glycol, polyethylene glycol, glycerin or mixtures thereof. In certain embodiments, the polyol is glycerin. In other embodiments, the polyol is a combination of polyols such as glycerin and propylene glycol or glycerin and sorbitol.

The polyol (or combinations thereof) can optionally, be present in the composition of the present invention at concentrations of from about 0.2% w/v to about 2.0% w/v, optionally from about 0.2% w/v to about 1.7% w/v, or optionally from about 0.4% w/v to about 1.5% w/v of the total composition.

Preservative Effectiveness Test

The compositions of the present invention meet the requirements of the preservative efficacy test as described in the EUROPEAN PHARMACOPOEIA 8.0 (EUROPEAN PHARMACOPOEIA 8.0, 5.1.3. Efficacy of Antimicrobial Preservation) (hereinafter to be referred to as "EP-B Criteria"). EP-B criteria requires that the viable cell count of bacteria (*Staphylococcus aureus, Escherichia coli* and *Pseudomonas aeruginosa*) at least 1.0 log reduction from the initial calculated count at 24 hours, at least 3.0 log reduction at 7 days from the previous value measured and not more than 0.5 log increase from the previous value measured (i.e., no increase) at 28 days, and the viable cell count of fungi (*Candida albicans* and *Aspergillus brasiliensis*) at least 1.0 log reduction from the initial calculated count at 14 days and no increase at 28 days from the previous measured value. The satisfaction criteria of the EP B Criteria is summarized in Table A.

TABLE A

Satisfaction of the Preservative Efficacy Test Under EP B Criteria
Log CFU/mL reduction

| Organisms | 6 h | 24 h | 7 d | 14 d | 28 d |
| --- | --- | --- | --- | --- | --- |
| Bacteria | | | | | |
| E. coli | — | 1 | 3 | — | NI* |
| S. aureus | | | | | |
| Ps. aeruginosa | | | | | |
| Yeast, Mold and Fungi | | | | | |
| C. albicans | — | — | — | 1 | NI* |
| A. brasiliensis | | | | | |

*NI; no increase in number of viable microorganisms compared to the previous reading The operation method of the preservative efficacy test described in the EUROPEAN PHARMACOPOEIA 8.0 includes the operation steps (i)-(v) (below) and the following bacteria as test microorganisms:

1. *Pseudomonas aeruginosa*: (Bacteria; ATCC 9027; NCIMB 8626; CIP 82.118)
2. *Staphylococcus aureus*: (Bacteria; ATCC 6538; NCTC 10788)
3. *Candida albicans*: (Yeast; ATCC10231; NCPF 3179; IP 48.72)
4. *Aspergillus brasiliensis*: (Mold; ATCC 16404; IMI 1490076; IP 1431.83)

Where necessary, microorganisms such as *Escherichia coli* and the like can be added as the test microorganism.

(i) The above-mentioned 5 kinds of microorganism strains to be used for the test are inoculated on the surface of a slant agar medium and precultured. As the agar medium for preculture, a casein soya bean digest agar medium is used for bacteria and a Sabouraud glucose agar medium is used for fungi. Bacteria are precultured at 30-35° C. for 18-24 hr, *Candida albicans* is precultured at 20-25° C. for 40-48 hr, and *Aspergillus brasiliensis* is precultured at 20-25° C. for 1 week or until good sporulation is achieved.

(ii) The bacterial and *C. albicans* cultures are harvested suing a sterile suspending fluid containing 9 g/L of sodium chloride R, adjusting the microbial count to about 108 micro-organisms per milliliter. To harvest the *A. brasiliensis* cultures, a sterile suspending fluid containing 9 g/L of sodium chloride R and 0.5 g/L polysorbate 80 is used, adjusting the microbial count to about 108 micro-organisms per milliliter.

(iii) Suitable samples of the harvested culture suspensions (ii) are removed and the number of colony-forming units per milliliter in each suspension is determined by plated count or membrane filtration. This value serves to determine the inoculum micro-organism count and the baseline for the test.

(iv) Samples of the compositions to be tested are transferred into a sterile cup containing a 0.22 micron sterilizing filter (such as a Durapore® filter (polyvinylidene fluoride) situated above a tightly sealed receiving vessel. Using a laboratory vacuum pump (such as a GAST non lubricating pump) approximately 250 mm Hg differential vacuum is applied through a sterile air filter opening in the receiving vessel to transfer the sample compositions through the sterilizing filter into the sterile receiving vessel.

(v) Samples of filtered compositions of (iv) are dispensed to separate sterilized containers. The sample compositions are inoculated with the test microorganism of (ii)

at 105-106 cells/mL and mixed thoroughly (to homogeneity) to prepare a mixed sample. The mixed sample is preserved at 20-25° C. with protection from light. (The volume of the inoculum suspension of (i) should not exceed 1% of the volume of the sample composition).

(vi) After preservation of the mixed samples of (v) for 24 hours from the start of the preservation, suitable samples are removed from each container, at "zero" hours (after the 24 hour preservation period), and at appropriate intervals thereafter according to the microorganism being assessed and the number of colony-forming units per milliliter in each mixed sample is determined by plated count or membrane filtration. (Residual antimicrobial activity of the sample compositions should be eliminated by dilution, filtration or use of a specific inactivator.)

After the operation of the above-mentioned (i)-(vi), when the viable cell counts of all the above-mentioned bacteria (*Staphylococcus aureus, Escherichia coli* and *Pseudomonas aeruginosa*) in the mixed solution decrease by 1 log or more 24 hr after inoculation, decrease by 3 log or more 7 days after inoculation, and do not increase 28 days after inoculation from the level of 7 days after inoculation, and the viable cell counts of fungi (*Candida albicans* and *Aspergillus brasiliensis*) decrease by 1 log or more 14 days after inoculation and do not increase 28 days after inoculation from the level of 14 days after inoculation, the criteria of the EP B Criteria preservative efficacy test is satisfied.

Optional Components

The compositions of the present invention may optionally comprise one or more additional excipients and/or one or more additional active ingredients. Excipients commonly used include, but are not limited to, demulcents, tonicity agents, preservatives, chelating agents, buffering agents (other than and in addition to the organic acids of the present invention), and surfactants. Other excipients comprise solubilizing agents, stabilizing agents, comfort-enhancing agents, polymers, emollients, pH-adjusting agents (other than and in addition to the organic acids of the present invention), and/or lubricants. Any of a variety of excipients may be used in the compositions of the present invention including water, mixtures of water and water-miscible solvents, such as vegetable oils or mineral oils comprising from 0.5% to 5% non-toxic water-soluble polymers, natural products, such as agar and acacia, starch derivatives, such as starch acetate and hydroxypropyl starch, and also other synthetic products such as polyvinyl alcohol, polyvinylpyrrolidone, polyvinyl methyl ether, polyethylene oxide, and preferably cross-linked polyacrylic acid and mixtures thereof.

Demulcents or soothing agents used with embodiments of the present invention include, but are not limited to, cellulose derivatives (such hydroxyethyl cellulose, methyl cellulose, hypromellose or mixtures thereof), glycerin, polyvinyl pyrrolidone, polyethylene oxide, polyethylene glycol, propylene glycol and polyacrylic acid. In certain embodiments, propylene glycol and polyethylene glycol 400 are the demulcents. In certain embodiments, glycerin, in addition to its use as a tonicity adjusting agent, can also act as a demulcent.

Suitable tonicity-adjusting agents include, but are not limited to, mannitol, sodium chloride, glycerin, and the like. Suitable buffering agents include, but are not limited to, phosphates, borates, acetates and the like, and amino alcohols such as 2-amino-2-methyl-1-propanol (AMP), salts of any of the above and mixtures of any of the above mentioned agents. Suitable surfactants include, but are not limited to, ionic and nonionic surfactants (though nonionic surfactants are preferred), RLM 100, POE 20 cetylstearyl ethers such as Procol® CS20, poloxamers such as Pluronic® F68, and block copolymers such as poly(oxyethylene)-poly(oxybutylene) compounds set forth in U.S. Patent Application Publication No. 2008/0138310 entitled "Use of PEO-PBO Block Copolymers in Ophthalmic Compositions" filed Dec. 10, 2007 (which publication is herein incorporated by reference).

Compositions of the present invention are ophthalmically suitable for application to a subject's eyes. The term "aqueous" typically denotes an aqueous formulation wherein the excipient is greater than about 50%, optionally greater than about 75%, or optionally greater than about 90% by weight water. These drops may be delivered from a single dose ampoule which may preferably be sterile and thus render microcidal or bacteriostatic/fungistatic components of the formulation unnecessary. Alternatively, the drops may be delivered from a multi-dose bottle which may preferably comprise a device which extracts any preservative from the composition as it is delivered, such devices being known in the art.

In certain embodiments, the compositions of the present invention are isotonic, or slightly hypotonic in order to combat any hypertonicity of tears caused by evaporation and/or disease. This may require a tonicity agent to bring the osmolality of the formulation to a level at or near 210-320 milliosmoles per kilogram (mOsm/kg). The compositions of the present invention generally have an osmolality in the range of 220-320 mOsm/kg, or, optionally, have an osmolality in the range of 235-300 mOsm/kg. The ophthalmic compositions will generally be formulated as sterile aqueous solutions.

The compositions of the present invention can also be used to administer pharmaceutically active compounds. Such compounds include, but are not limited to, (or selected from or selected from the group consisting of) glaucoma therapeutics, pain relievers, anti-inflammatory, vaso-constrictors, dry eye relievers and anti-allergy medications, and anti-infectives. More specific examples of pharmaceutically active compounds include betaxolol, timolol, pilocarpine or pharmaceutically acceptable salts thereof; carbonic anhydrase inhibitors or pharmaceutically acceptable salts thereof; prostglandins; dopaminergic antagonists; post-surgical antihypertensive agents, such as para-amino clonidine (apraclonidine) or pharmaceutically acceptable salts thereof; anti-infectives such as ciprofloxacin, moxifloxacin, tobramycin or pharmaceutically acceptable salts thereof; non-steroidal and steroidal anti-inflammatories, such as naproxen, diclofenac, nepafenac, suprofen, ketorolac, tetrahydrocortisol, dexamethasone or pharmaceutically acceptable salts thereof; dry eye therapeutics or pharmaceutically acceptable salts thereof such as PDE4 inhibitors; vaso-contrictors such as tetrahydrozoline, naphazoline, oxymetazoline, ephedrine, phenylephrine or pharmaceutically acceptable salts thereof; anti-allergy medications or pharmaceutically acceptable salts thereof such as H1/H4 inhibitors, H4 inhibitors, olopatadine; and dry eye relievers such as tamarind seed extract, hyaluronic acid and guar gum (including high performance guar gum); or mixtures of any of the above mentioned actives or categories of actives.

It is also contemplated that the concentrations of the ingredients comprising the formulations of the present invention can vary. A person of ordinary skill in the art would understand that the concentrations can vary depending on the addition, substitution, and/or subtraction of ingredients in a given formulation.

In certain embodiments, the compositions of the present invention are buffered, using buffering agents, such that the compositions maintain a pH of from about 5.0 to a pH of about 8.0, optionally a pH of from about 6.5 to a pH of about 8.0. Topical formulations (particularly topical ophthalmic formulations, as noted above) are preferred which have a physiological pH matching the tissue to which the formulation will be applied or dispensed.

In certain embodiments, the compositions of the present invention is in the form of eye-drop solution, eye wash solution, contact lens lubricating and/or rewetting solution, spray, mist or any other manner of administering a composition to the eye.

In particular embodiments, the composition of the present invention are formulated for administration at any frequency of administration, including once a week, once every five days, once every three days, once every two days, twice a day, three times a day, four times a day, five times a day, six times a day, eight times a day, every hour, or greater frequency. Such dosing frequency is also maintained for a varying duration of time depending on the therapeutic needs of the user. The duration of a particular therapeutic regimen may vary from one-time dosing to a regimen that extends for months or years. One of ordinary skill in the art would be familiar with determining a therapeutic regimen for a specific indication.

EXAMPLES

The compositions of the present invention as described in following examples illustrate specific embodiments of compositions of the present invention, but are not intended to be limiting thereof. Other modifications can be undertaken by the skilled artisan without departing from the spirit and scope of this invention.

TABLE 1

Examples of the Compositions of the Present Invention

| INGREDIENT | 1A Useful for Relief of Eye Irritation | | 1B Useful for Relief of Eye Irritation | | 1C Useful for Relief of Eye Irritation | | 1D Useful for Relief of Dry Eye | |
|---|---|---|---|---|---|---|---|---|
| | % w/w | amount per batch (gms) | % w/w | amount per batch (gms) | % w/w | amount per batch (gms) | % w/w | amount per batch (gms) |
| Tetrahydrozoline Hydrochloride | 0.05 (or may us about 0.05) | 0.50 (or may use about 0.50) | 0.05 (or may use about 0.05) | 0.50 (or may use about 0.50) | 0.05 (or may use about 0.05) | 0.50 (or may use about 0.50) | — | — |
| Polyethylene Glycol 400 | — | — | 1.12 (or may use about 1.12) | 11.2 (or may use about 11.2) | 1.12 (or may use about 1.12) | 11.2 (or may use about 11.2) | 1.12 (or may use about 1.12) | 11.2 (or may use about 11.2) |
| Glycerin | 0.50 (or may use about 0.50) | 5.0 (or may use about 5.0) | 0.25 (or may use about 0.25) | 2.5 (or may use about 2.5) | 0.25 (or may use about 0.25) | 2.5 (or may use about 2.5) | 0.25 (or may use about 0.25) | 2.5 (or may use about 2.5) |
| Hypromellose E3 2910 | — | — | 0.20 (or may use about 0.20) | 2.0 (or may use about 2.0) | — | — | 0.20 (or may use about 0.20) | 2.0 (or may use about 2.0) |
| Hypromellose E4M 2910 | — | — | — | — | 0.36 (or may use about 0.36) | 3.6 (or may use about 3.6) | — | — |
| Boric Acid | 0.52 (or may use about 0.52) | 5.2 (or may use about 5.2) | 0.52 (or may use about 0.52) | 5.2 (or may use about 5.2) | 0.52 (or may use about 0.52) | 5.2 (or may use about 5.2) | 0.52 (or may use about 0.52) | 5.2 (or may use about 5.2) |
| Sodium Borate | 0.06 (or may use about 0.06) | 0.6 (or may use about 0.6) | 0.06 (or may use about 0.06) | 0.6 (or may use about 0.6) | 0.06 (or may use about 0.06) | 0.6 (or may use about 0.6) | 0.06 (or may use about 0.06) | 0.6 (or may use about 0.6) |
| Disodium Phosphate | 0.027 (or may use about 0.027) | 0.27 (or may use about 0.27) | 0.027 (or may use about 0.027) | 0.27 (or may use about 0.27) | 0.027 (or may use about 0.027) | 0.27 (or may use about 0.27) | 0.027 (or may use about 0.027) | 0.27 (or may use about 0.27) |
| Sodium Citrate Dihydrate | 0.0009 (or may use about 0.0009) | 0.009 (or may use about 0.009) | 0.0009 (or may use about 0.0009) | 0.009 (or may use about 0.009) | 0.0009 (or may use about 0.0009) | 0.009 (or may use about 0.009) | 0.0009 (or may use about 0.0009) | 0.009 (or may use about 0.009) |
| Potassium Chloride | 0.18 (or may use about 0.18) | 1.8 (or may use about 1.8) | 0.18 (or may use about 0.18) | 1.8 (or may use about 1.8) | 0.18 (or may use about 0.18) | 1.8 (or may use about 1.8) | 0.18 (or may use about 0.18) | 1.8 (or may use about 1.8) |
| Sodium Chloride | 0.15 (or may use about 0.15) | 1.5 (or may use about 1.5) | 0.12 (or may use about 0.12) | 1.2 (or may use about 1.2) | 0.12 (or may use about 0.12) | 1.2 (or may use about 1.2) | 0.12 (or may use about 0.12) | 1.2 (or may use about 1.2) |

TABLE 1-continued

Examples of the Compositions of the Present Invention

| INGREDIENT | 1A Useful for Relief of Eye Irritation | | 1B Useful for Relief of Eye Irritation | | 1C Useful for Relief of Eye Irritation | | 1D Useful for Relief of Dry Eye | |
|---|---|---|---|---|---|---|---|---|
| | % w/w | amount per batch (gms) | % w/w | amount per batch (gms) | % w/w | amount per batch (gms) | % w/w | amount per batch (gms) |
| 50% Aqueous Solution of Sodium Lactate | 0.057 (or may use about 0.057) | 0.57 (or may use about 0.57) | 0.056 (or may use about 0.056) | 0.56 (or may use about 0.56) | 0.056 (or may use about 0.056) | 0.56 (or may use about 0.56) | 0.056 (or may use about 0.056) | 0.56 (or may use about 0.56) |
| Magnesium Chloride | 0.013 (or may use about 0.013) | 0.13 (or may use about 0.13) | 0.013 (or may use about 0.013) | 0.13 (or may use about 0.13) | 0.013 (or may use about 0.013) | 0.13 (or may use about 0.13) | 0.013 (or may use about 0.013) | 0.13 (or may use about 0.13) |
| Glucose | 0.004 (or may use about 0.004) | 0.04 (or may use about 0.04) | 0.004 (or may use about 0.004) | 0.04 (or may use about 0.04) | 0.004 (or may use about 0.004) | 0.04 (or may use about 0.04) | 0.004 (or may use about 0.004) | 0.04 (or may use about 0.04) |
| Glycine | 0.00002 (or may use about 0.00002) | 0.0002 (or may use about 0.0002) | 0.00002 (or may use about 0.00002) | 0.0002 (or may use about 0.0002) | 0.00002 (or may use about 0.00002) | 0.0002 (or may use about 0.0002) | 0.00002 (or may use about 0.00002) | 0.0002 (or may use about 0.0002) |
| Ascorbic Acid | 0.00001 (or may use about 0.00001) | 0.0001 (or may use about 0.0001) | 0.00001 (or may use about 0.00001) | 0.0001 (or may use about 0.0001) | 0.00001 (or may use about 0.00001) | 0.0001 (or may use about 0.0001) | 0.00001 (or may use about 0.00001) | 0.0001 (or may use about 0.0001) |
| Polyquaternium 42 | 0.003 (or may use about 0.003) | 0.030 (or may use about 0.030) | 0.003 (or may use about 0.003) | 0.030 (or may use about 0.030) | 0.003 (or may use about 0.003) | 0.030 (or may use about 0.030) | 0.003 (or may use about 0.003) | 0.030 (or may use about 0.030) |
| Purified Water | 98.440 | 984.40 | 97.400 | 974.00 | 97.240 | 972.40 | 97.450 | 974.50 |
| total | 100.00% | 1000.00 g | 100.00% | 1000.00 g | 100.00% | 1000.00 g | 100.00% | 1000.00 g |

For Examples 1A-6D

The Tetrahydrozoline Hydrochloride was supplied by PCAS (TURKU, FINLAND). The Polyethylene Glycol 400 was supplied by Clariant Produkte (BURGKIRCHEN, GERMANY). The Glycerin was supplied by Emery Oleochemicals GmbH (DUSSELDORF, GERMANY). The Hypromellose E3 2910 and Hypromellose E4M were supplied by DOW CHEMICAL (PLAQUEMINE, La., USA). The Boric Acid was supplied by Merck KGaA (DARMSTADT, GERMANY). The Sodium Borate was supplied by Merck KGaA (DARMSTADT, GERMANY). The Disodium Phosphate was supplied by KGaA (DARMSTADT, GERMANY). The Sodium Citrate was supplied by Merck KGaA (DARMSTADT, GERMANY). The Potassium Chloride was supplied by Merck KGaA (DARMSTADT, GERMANY). The Sodium Chloride was supplied by Caldic (GERMANY). The Sodium Lactate was supplied as Sodium Lactate (50% aqueous) by Merck KGaA (DARMSTADT, GERMANY). The Magnesium Chloride was supplied by Merck KGaA (DARMSTADT, GERMANY). The Glucose was supplied by Roquette Freres (LASTREM, FRANCE). The Glycine was supplied by Merck KGaA (DARMSTADT, GERMANY). The Ascorbic Acid was supplied by DSM NUTRITIONAL Products (DRAKEMYRE, SCOTLAND, UK). The Polyquaternium 42 was supplied as Polyquaternium 42 (33% aqueous) by DSM BIOMEDICAL, (BERKELEY, Calif.).

The procedure for preparing solution 1A was as follows:

1. To a 250 ml beaker 0.90 grams of Sodium Citrate Dihydrate was added to 95 grams of Purified Water USP. The solution was mixed until the Sodium Citrate Dihydrate dissolved.
2. To the above were added 0.02 grams of Glycine and 0.01 grams of Ascorbic acid. The solution was mixed until the Glycine and Ascorbic acid dissolved.
3. An additional 4.07 grams of water was added and mixed until the solution was uniform.
4. In a separate a container, 1.0 gram of the solution of Step 2 is slowly added to 930 g of water at a temperature of 20° C. to 30° C. while mixing.
5. To the solution of Step 4 were added the following ingredients while mixing, allowing time for each to dissolve completely before adding the next: 0.27 grams of Disodium Phosphate, 0.13 grams of Magnesium Chloride, 1.80 grams of Potassium Chloride, 0.04 grams of Glucose, 0.57 grams of Sodium Lactate and 5.0 grams of Glycerin.
6. To the solution of Step 5, 5.2 grams of Boric acid was slowly added while mixing and mixed until completely dissolved.
7. To the solution of Step 6, were added the following ingredients while mixing, allowing time for each to dissolve completely before adding the next: 0.60 grams of Sodium Borate, 0.50 grams of Tetrahydrozoline Hydrochloride, 1.5 grams of Sodium Chloride and 0.09 grams of a 33% solution of Polyquaternium 42 in water.
8. On completion of addition of all ingredients, additional water is added to bring the weight of the solution to a total of 1,000.00 grams and the solution is mixed for an additional 10 minutes.
9. The solution is filtered through a sterile 0.22 micron filter.

The procedure for preparing solution 1B was as follows:
1. To a 250 ml beaker 0.90 grams of Sodium Citrate Dihydrate was added to 95 grams of Purified Water USP. The solution was mixed until the Sodium Citrate Dihydrate dissolved.
2. To the solution of Step 1 were added 0.02 grams of Glycine and 0.01 grams of Ascorbic acid. The solution was mixed until the Glycine and Ascorbic acid dissolved.
3. An additional 4.07 grams of water was added and mixed until the solution was uniform.
4. In a separate a container, 2.0 grams of Hypromellose E3 2910 was slowly added to 930 g of water at a temperature of 20° C. to 30° C. while mixing. The solution was mixed until all of the Hypromellose E3 2910 is completely dispersed and dissolved.
5. To the solution of Step 4 were added 11.2 grams of Polyethylene Glycol 400 and 2.5 grams of Glycerin while mixing to dissolve.
6. To the solution of Step 5 was added 1.0 grams of the solution of Step 2 while mixing to dissolve.
7. To the solution of Step 6 were added the following ingredients while mixing, allowing time for each to dissolve completely before adding the next: 0.27 grams of Disodium Phosphate, 0.13 grams of Magnesium Chloride, 1.80 grams of Potassium Chloride, 0.04 grams of Glucose, and 0.56 grams of Sodium Lactate.
8. To the solution of Step 7, 5.2 grams of Boric acid was slowly added while mixing and mixed until completely dissolved.
9. To the solution of Step 8, were added the following ingredients while mixing, allowing time for each to dissolve completely before adding the next: 0.60 grams of Sodium Borate, 0.50 grams of Tetrahydrozoline Hydrochloride, 1.2 grams of Sodium Chloride and 0.09 grams of a 33% solution of Polyquaternium 42 in water.
10. On completion of addition of all ingredients, additional water is added to bring the weight of the solution to a total of 1,000.00 grams and the solution is mixed for an additional 10 minutes.
11. The solution is filtered through a sterile 0.22 micron filter.

The procedure for preparing solution 1C was as follows:
1. To a 250 ml beaker 0.90 grams of Sodium Citrate Dihydrate was added to 95 grams of Purified Water USP. The solution was mixed until the Sodium Citrate Dihydrate dissolved.
2. To the solution of Step 1 were added 0.02 grams of Glycine and 0.01 grams of Ascorbic acid. The solution was mixed until the Glycine and Ascorbic acid dissolved.
3. An additional 4.07 grams of water was added and mixed until the solution was uniform.
4. In a separate a container, 3.6 grams of Hypromellose E4M 2910 was slowly added to 800 g of water at a temperature of 80° C. to 85° C. while mixing. When the addition is completed, the solution was mixed for an additional 30 minutes at a temperature of 80° C. to 85° C. until all of the Hypromellose E4M 2910 was completely dispersed and dissolved.
5. Heat is removed from the solution of step 4 and the solution is allowed to cool to ambient temperature (20° C. to 30° C.) while mixing.
6. To the solution of Step 5 were added 11.2 grams of Polyethylene Glycol 400 and 2.5 grams of Glycerin while mixing to dissolve.
7. To the solution of Step 6 was added 1.0 grams of the solution of Step 2 while mixing to dissolve.
8. To the solution of Step 7 were added the following ingredients while mixing, allowing time for each to dissolve completely before adding the next: 0.27 grams of Disodium Phosphate, 0.13 grams of Magnesium Chloride, 1.80 grams of Potassium Chloride, 0.04 grams of Glucose, and 0.56 grams of Sodium Lactate.
9. To the solution of Step 8, 5.2 grams of Boric acid was slowly added while mixing and mixed until completely dissolved.
10. To the solution of Step 9, were added the following ingredients while mixing, allowing time for each to dissolve completely before adding the next: 0.60 grams of Sodium Borate, 0.50 grams of Tetrahydrozoline Hydrochloride, 1.2 grams of Sodium Chloride and 0.09 grams of a 33% solution of Polyquaternium 42 in water.
11. On completion of addition of all ingredients, additional water is added to bring the weight of the solution to a total of 1,000.00 grams and the solution is mixed for an additional 10 minutes.
12. The solution is filtered through a sterile 0.22 micron filter.

The procedure for preparing solution 1D was as follows:
1. To a 250 ml beaker 0.90 grams of Sodium Citrate Dihydrate was added to 95 grams of Purified Water USP. The solution was mixed until the Sodium Citrate Dihydrate dissolved.
2. To the solution of Step 1 were added 0.02 grams of Glycine and 0.01 grams of Ascorbic acid. The solution was mixed until the Glycine and Ascorbic acid dissolved.
3. An additional 4.07 grams of water was added and mixed until the solution was uniform.
4. In a separate a container, 2.0 grams of Hypromellose E3 2910 was slowly added to 930 g of water at a temperature of 20° C. to 30° C. while mixing. The solution was mixed until all of the Hypromellose E3 2910 is completely dispersed and dissolved.
5. To the solution of Step 4 were added 11.2 grams of Polyethylene Glycol 400 and 2.5 grams of Glycerin while mixing to dissolve.
6. To the solution of Step 5 was added 1.0 grams of the solution of Step 2 while mixing to dissolve.
7. To the solution of Step 6 were added the following ingredients while mixing, allowing time for each to dissolve completely before adding the next: 0.27 grams of Disodium Phosphate, 0.13 grams of Magnesium Chloride, 1.80 grams of Potassium Chloride, 0.04 grams of Glucose, and 0.56 grams of Sodium Lactate.
8. To the solution of Step 7, 5.2 grams of Boric acid was slowly added while mixing and mixed until completely dissolved.
9. To the solution of Step 8, were added the following ingredients while mixing, allowing time for each to dissolve completely before adding the next: 0.60 grams of Sodium Borate, 1.2 grams of Sodium Chloride and 0.09 grams of a 33% solution of Polyquaternium 42 in water.
10. On completion of addition of all ingredients, additional water is added to bring the weight of the solution to a total of 1,000.00 grams and the solution is mixed for an additional 10 minutes.
11. The solution is filtered through a sterile 0.22 micron filter.

TABLE 2

Examples of the Compositions of the Present Invention

| INGREDIENT | 2A % w/w | 2A amount per batch (gms) | 2B % w/w | 2B amount per batch (gms) |
|---|---|---|---|---|
| Tetrahydrozoline Hydrochloride | 0.05 | 0.50 | 0.05 | 0.50 |
| Polyethylene Glycol 400 | 0.40 | 4.0 | — | — |
| Polysorbate 80 | — | — | 1.0 | 10.0 |
| Propylene Glycol | 0.30 | 3.0 | — | — |
| Sodium CMC | 0.6 | 6.0 | 0.6 | 6.0 |
| Boric Acid | 0.52 | 5.2 | 0.52 | 5.2 |
| Sodium Borate | 0.06 | 0.6 | 0.06 | 0.6 |
| Disodium Phosphate | 0.027 | 0.27 | 0.027 | 0.27 |
| Sodium Citrate | 0.0009 | 0.009 | 0.0009 | 0.009 |
| Potassium Chloride | 0.18 | 1.8 | 0.18 | 1.8 |
| Sodium Chloride | 0.10 | 1.0 | 0.26 | 2.6 |
| 50% Aqueous Solution of Sodium Lactate | 0.056 | 0.56 | 0.056 | 0.56 |
| Magnesium Chloride | 0.013 | 0.13 | 0.013 | 0.13 |
| Glucose | 0.004 | 0.04 | 0.004 | 0.04 |
| Glycine | 0.00002 | 0.0002 | 0.00002 | 0.0002 |
| Ascorbic Acid | 0.00001 | 0.0001 | 0.00001 | 0.0001 |
| Polyquaternium 42 | 0.003 | 0.030 | 0.003 | 0.030 |
| Purified Water | 97.69 | 976.90 | 97.30 | 973.0 |
| total | 100.00% | 1000.00 g | 100.00% | 1000.00 g |

For Examples 2A-2B

The Tetrahydrozoline Hydrochloride was supplied by PCAS (TURKU, FINLAND). The Polyethylene Glycol 400 was supplied by Clariant Produkte (BURGKIRCHEN, GERMANY). The Polysorbate 80 and Propylene Glycol were supplied by Spectrum (USA). The Sodium Carboxymethylcellulose (CMC) was supplied by DOW CHEMICAL (PLAQUEMINE, La., USA). The Boric Acid was supplied by Merck KGaA (DARMSTADT, GERMANY). The Sodium Borate was supplied by Merck KGaA (DARMSTADT, GERMANY). The Disodium Phosphate was supplied by KGaA (DARMSTADT, GERMANY). The Sodium Citrate was supplied by Merck KGaA (DARMSTADT, GERMANY). The Potassium Chloride was supplied by Merck KGaA (DARMSTADT, GERMANY). The Sodium Chloride was supplied by Caldic (DUSSELDORF, GERMANY). The Sodium Lactate was supplied as Sodium Lactate (50% aqueous) by Merck KGaA (DARMSTADT, GERMANY). The Magnesium Chloride was supplied by Merck KGaA (DARMSTADT, GERMANY). The Glucose was supplied by Roquette Freres (LASTREM, FRANCE). The Glycine was supplied by Merck KGaA (DARMSTADT, GERMANY). The Ascorbic Acid was supplied by DSM NUTRITIONAL Products (DRAKEMYRE, SCOTLAND, UK). The Polyquaternium 42 was supplied as Polyquaternium 42 (33% aqueous) by DSM BIOMEDICAL, (BERKELEY, Calif.).

The procedure for preparing solution 2A was as follows:
1. To a 250 ml beaker 0.90 grams of Sodium Citrate Dihydrate was added to 95 grams of Purified Water USP. The solution was mixed until the Sodium Citrate Dihydrate dissolved.
2. To the solution of Step 1 were added 0.02 grams of Glycine and 0.01 grams of Ascorbic acid. The solution was mixed until the Glycine and Ascorbic acid dissolved.
3. An additional 4.07 grams of water was added and mixed until the solution was uniform.
4. In a separate a container, 6.0 grams of Sodium Carboxymethylcellulose was slowly added to 930 g of water at a temperature of 20° C. to 30° C. while mixing. The solution was mixed until all of the Sodium Carboxymethylcellulose is completely dispersed and dissolved.
5. To the solution of Step 4 were added 4.0 grams of Polyethylene Glycol 400 and 3.0 grams of Propylene Glycol while mixing to dissolve.
6. To the solution of Step 5 was added 1.0 grams of the solution of Step 3 while mixing to dissolve.
7. To the solution of Step 6 were added the following ingredients while mixing, allowing time for each to dissolve completely before adding the next: 0.27 grams of Disodium Phosphate, 0.13 grams of Magnesium Chloride, 1.80 grams of Potassium Chloride, 0.04 grams of Glucose, and 0.56 grams of Sodium Lactate.
8. To the solution of Step 7, 5.2 grams of Boric acid was slowly added while mixing and mixed until completely dissolved.
9. To the solution of Step 8, were added the following ingredients while mixing, allowing time for each to dissolve completely before adding the next: 0.60 grams of Sodium Borate, 0.50 grams of Tetrahydrozoline Hydrochloride, 1.0 gram of Sodium Chloride and 0.09 grams of a 33% solution of Polyquaternium 42 in water.
10. On completion of addition of all ingredients, additional water is added to bring the weight of the solution to a total of 1,000.00 grams and the solution is mixed for an additional 10 minutes.
11. The solution is filtered through a sterile 0.22 micron filter.

The procedure for preparing solution 2B was as follows:
1. To a 250 ml beaker 0.90 grams of Sodium Citrate Dihydrate was added to 95 grams of Purified Water USP. The solution was mixed until the Sodium Citrate Dihydrate dissolved.
2. To the solution of Step 1 were added 0.02 grams of Glycine and 0.01 grams of Ascorbic acid. The solution was mixed until the Glycine and Ascorbic acid dissolved.
3. An additional 4.07 grams of water was added and mixed until the solution was uniform.
4. In a separate a container, 6.0 grams of Sodium Carboxymethylcellulose was slowly added to 930 g of water at a temperature of 20° C. to 30° C. while mixing. The solution was mixed until all of the Sodium Carboxymethylcellulose is completely dispersed and dissolved.
5. To the solution of Step 4 was added 10.0 grams of Polysorbate 80 while mixing to dissolve.
6. To the solution of Step 5 was added 1.0 grams of the solution of Step 3 while mixing to dissolve.
7. To the solution of Step 6 were added the following ingredients while mixing, allowing time for each to dissolve completely before adding the next: 0.27 grams of Disodium Phosphate, 0.13 grams of Magnesium Chloride, 1.80 grams of Potassium Chloride, 0.04 grams of Glucose, and 0.56 grams of Sodium Lactate.

8. To the solution of Step 7, 5.2 grams of Boric acid was slowly added while mixing and mixed until completely dissolved.
9. To the solution of Step 8, were added the following ingredients while mixing, allowing time for each to dissolve completely before adding the next: 0.60 grams of Sodium Borate, 0.50 grams of Tetrahydrozoline Hydrochloride, 2.6 grams of Sodium Chloride and 0.09 grams of a 33% solution of Polyquaternium 42 in water.
10. On completion of addition of all ingredients, additional water is added to bring the weight of the solution to a total of 1,000.00 grams and the solution is mixed for an additional 10 minutes.
11. The solution is filtered through a sterile 0.22 micron filter.

USA). The Boric Acid can be supplied by Merck KGaA (DARMSTADT, GERMANY). The Sodium Borate can be supplied by Merck KGaA (DARMSTADT, GERMANY). The Disodium Phosphate can be supplied by KGaA (DARMSTADT, GERMANY). The Sodium Citrate can be supplied by Merck KGaA (DARMSTADT, GERMANY). The Potassium Chloride can be supplied by Merck KGaA (DARMSTADT, GERMANY). The Sodium Chloride can be supplied by Caldic (DUSSELDORF, GERMANY). The Sodium Lactate can be supplied as Sodium Lactate (50% aqueous) by Merck KGaA (DARMSTADT, GERMANY). The Magnesium Chloride can be supplied by Merck KGaA (DARMSTADT, GERMANY). The Glucose can be supplied by Roquette Freres (LASTREM, FRANCE). The Glycine can be supplied by Merck KGaA (DARMSTADT,

TABLE 3

Prophetic Ophthalmic Solutions of the Present invention

| INGREDIENT | 3A % w/w | 3A amount per batch (gms) | 3B % w/w | 3B amount per batch (gms) | 3C % w/w | 3C amount per batch (gms) | 3D % w/w | 3D amount per batch (gms) | 3E % w/w | 3E amount per batch (gms) |
|---|---|---|---|---|---|---|---|---|---|---|
| Tetrahydrozoline Hydrochloride | 0.05 | 0.50 | — | — | 0.05 | 0.50 | — | — | — | — |
| Naphazoline Hydrochloride | — | — | — | — | — | — | — | — | 0.025 | 0.25 |
| Pheniramine Maleate | — | — | — | — | — | — | — | — | 0.3 | 3.0 |
| Polyethylene Glycol 400 | 1.12 | 11.2 | — | — | — | — | 1.12 | 11.2 | 1.12 | 1.12 |
| Glycerin | 0.25 | 2.5 | — | — | 0.25 | 2.5 | 0.25 | 2.5 | — | — |
| Polysorbate 80 | — | — | 0.60 | 6.0 | — | — | — | — | — | — |
| Propylene Glycol | — | — | 0.30 | 3.0 | — | — | — | — | 0.30 | 3.0 |
| Hypromellose E4M 2910 | 0.36 | 3.6 | — | — | 0.36 | 3.6 | 0.20 | 2.0 | — | — |
| Boric Acid | 0.52 | 5.2 | 0.52 | 5.2 | 0.52 | 5.2 | 0.52 | 5.2 | 0.52 | 5.2 |
| Sodium Borate | 0.06 | 0.6 | 0.06 | 0.6 | 0.06 | 0.6 | 0.06 | 0.6 | 0.06 | 0.6 |
| Disodium Phosphate | 0.027 | 0.27 | 0.027 | 0.27 | 0.027 | 0.27 | — | — | 0.027 | 0.27 |
| Sodium Citrate | 0.0009 | 0.009 | 0.0009 | 0.009 | 0.0009 | 0.009 | 0.0009 | 0.009 | 0.0009 | 0.009 |
| Potassium Chloride | — | — | 0.18 | 1.8 | 0.18 | 1.8 | 0.18 | 1.8 | 0.18 | 1.8 |
| Sodium Chloride | 0.12 | 1.2 | — | — | 0.12 | 1.2 | — | — | 0.03 | 3.0 |
| 50% Aqueous Solution of Sodium Lactate | 0.056 | 0.56 | 0.056 | 0.56 | — | — | 0.056 | 0.56 | 0.056 | 0.56 |
| Magnesium Chloride | — | — | — | — | 0.013 | 0.13 | 0.013 | 0.13 | 0.013 | 0.13 |
| Glucose | — | — | 0.004 | 0.04 | 0.004 | 0.04 | 0.004 | 0.04 | 0.004 | 0.04 |
| Glycine | — | — | 0.00002 | 0.0002 | 0.00002 | 0.0002 | 0.00002 | 0.0002 | 0.00002 | 0.0002 |
| Ascorbic Acid | 0.00001 | 0.0001 | 0.00001 | 0.0001 | 0.00001 | 0.0001 | 0.00001 | 0.0001 | 0.00001 | 0.0001 |
| Polyquatemium 42 | 0.003 | 0.030 | 0.003 | 0.030 | 0.003 | 0.030 | 0.003 | 0.030 | 0.003 | 0.030 |
| Purified Water | 97.43 | 974.3 | 98.25 | 982.5 | 98.38 | 983.8 | 97.60 | 976.0 | 97.36 | 973.6 |
| Total | 100.00% | 1000.00 g | 100.00% | 1000.00 g | 100.00% | 1000.00 g | 100.00% | 1000.00 g | 100.00% | 1000.00 g |

For Examples 3A-3E

The Tetrahydrozoline Hydrochloride can be supplied by PCAS (TURKU, FINLAND). The Polyethylene Glycol 400 can be supplied by Clariant Produkte (BURGKIRCHEN, GERMANY). The Naphazoline Hydrochloride was supplied by LOBA Feinchemie (FISCHAMEND, AUSTRIA). The Pheniramine Maleate was supplied by Kongo Chemical Company (TOYAMA, JAPAN). The Glycerin can be supplied by Emery Oleochemicals GmbH (DUSSELDORF, GERMANY). The Polysorbate 80 and Propylene Glycol can be supplied by Spectrum (USA). Hypromellose E4M can be supplied by DOW CHEMICAL (PLAQUEMINE, La., USA). GERMANY). The Ascorbic Acid can be supplied by DSM NUTRITIONAL Products (DRAKEMYRE, SCOTLAND, UK). The Polyquaternium 42 can be supplied as Polyquaternium 42 (33% aqueous) by DSM BIOMEDICAL, (BERKELEY, Calif.).

The procedure for preparing solution 3A is as follows:
1. To a 250 ml beaker 0.90 grams of Sodium Citrate Dihydrate is added to 95 grams of Purified Water USP. The solution is mixed until the Sodium Citrate Dihydrate dissolved.
2. To the solution of Step 1 is added 0.01 grams of Ascorbic acid. The solution is mixed until the Ascorbic acid dissolved.

3. An additional 4.09 grams of water is added and mixed until the solution is uniform.
4. In a separate a container, 3.6 grams of Hypromellose E4M 2910 is slowly added to 800 g of water at a temperature of 80° C. to 85° C. while mixing. When the addition is completed, the solution is mixed for an additional 30 minutes at a temperature of 80° C. to 85° C. until all of the Hypromellose E4M 2910 is completely dispersed and dissolved.
5. Heat is removed from the solution of step 4 and the solution is allowed to cool to ambient temperature (20° C. to 30° C.) while mixing.
6. To the solution of Step 5 is added 2.5 grams of Glycerin while mixing to dissolve.
7. To the solution of Step 6 is added 1.0 grams of the solution of Step 3 while mixing to dissolve.
8. To the solution of Step 7 are added the following ingredients while mixing, allowing time for each ingredient to dissolve completely before adding the next: 0.27 grams of Disodium Phosphate and 0.56 grams of Sodium Lactate.
9. To the solution of Step 8, 5.2 grams of Boric acid is slowly added while mixing and mixed until completely dissolved.
10. To the solution of Step 9, are added the following ingredients while mixing, allowing time for each ingredient to dissolve completely before adding the next: 0.60 grams of Sodium Borate, 0.50 grams of Tetrahydrozoline Hydrochloride, 1.2 grams of Sodium Chloride and 0.09 grams of a 33% solution of Polyquaternium 42 in water.
11. On completion of addition of all ingredients, additional water is added to bring the weight of the solution to a total of 1,000.00 grams and the solution is mixed for an additional 10 minutes.
12. The solution is filtered through a sterile 0.22 micron filter.

It is expected that the above solution should satisfy EP B requirements for preservative efficacy.

The procedure for preparing solution 3B is as follows:
1. To a 250 ml beaker 0.90 grams of Sodium Citrate Dihydrate is added to 95 grams of Purified Water USP. The solution is mixed until the Sodium Citrate Dihydrate dissolved.
2. To the solution of Step 1 are added 0.02 grams of Glycine and 0.01 grams of Ascorbic acid. The solution is mixed until the Glycine and Ascorbic acid dissolved.
3. An additional 4.07 grams of water is added and mixed until the solution was uniform.
4. In a separate a container, 6.0 grams of Polysorbate 80 and 3.0 grams of Propylene Glycol are slowly added to 930 g of water at a temperature of 20° C. to 30° C. while mixing. The solution is mixed until both ingredients are completely dissolved.
5. To the solution of Step 4 is added 1.0 grams of the solution of Step 3 while mixing to dissolve.
6. To the solution of Step 5 are added the following ingredients while mixing, allowing time for each to dissolve completely before adding the next: 0.27 grams of Disodium Phosphate, 1.80 grams of Potassium Chloride, 0.04 grams of Glucose, and 0.56 grams of Sodium Lactate.
7. To the solution of Step 6, 5.2 grams of Boric acid is slowly added while mixing and mixed until completely dissolved.
8. To the solution of Step 7, are added the following ingredients while mixing, allowing time for each to dissolve completely before adding the next: 0.60 grams of Sodium Borate, 0.50 grams of Tetrahydrozoline Hydrochloride, and 0.09 grams of a 33% solution of Polyquaternium 42 in water.
9. On completion of addition of all ingredients, additional water is added to bring the weight of the solution to a total of 1,000.00 grams and the solution is mixed for an additional 10 minutes.
10. The solution is filtered through a sterile 0.22 micron filter.

It is expected that the above solution should satisfy EP B requirements for preservative efficacy.

The procedure for preparing solution 3C is as follows:
1. To a 250 ml beaker 0.90 grams of Sodium Citrate Dihydrate is added to 95 grams of Purified Water USP. The solution is mixed until the Sodium Citrate Dihydrate dissolved.
2. To the solution of Step 1 are added 0.02 grams of Glycine and 0.01 grams of Ascorbic acid. The solution is mixed until the Glycine and Ascorbic acid dissolved.
3. An additional 4.07 grams of water is added and mixed until the solution was uniform.
4. In a separate a container, 3.6 grams of Hypromellose E4M 2910 is slowly added to 800 g of water at a temperature of 80° C. to 85° C. while mixing. When the addition is completed, the solution is mixed for an additional 30 minutes at a temperature of 80° C. to 85° C. until all of the Hypromellose E4M 2910 is completely dispersed and dissolved.
5. Heat is removed from the solution of step 4 and the solution is allowed to cool to ambient temperature (20° C. to 30° C.) while mixing.
6. To the solution of Step 5 is added 2.5 grams of Glycerin while mixing to dissolve.
7. To the solution of Step 6 is added 1.0 grams of the solution of Step 3 while mixing to dissolve.
8. To the solution of Step 7 are added the following ingredients while mixing, allowing time for each to dissolve completely before adding the next: 0.27 grams of Disodium Phosphate, 0.13 grams of Magnesium Chloride, 1.80 grams of Potassium Chloride, and 0.04 grams of Glucose.
9. To the solution of Step 8, 5.2 grams of Boric acid is slowly added while mixing and mixed until completely dissolved.
10. To the solution of Step 9, are added the following ingredients while mixing, allowing time for each to dissolve completely before adding the next: 0.60 grams of Sodium Borate, 0.50 grams of Tetrahydrozoline Hydrochloride, 1.2 grams of Sodium Chloride and 0.09 grams of a 33% solution of Polyquaternium 42 in water.
11. On completion of addition of all ingredients, additional water is added to bring the weight of the solution to a total of 1,000.00 grams and the solution is mixed for an additional 10 minutes.
12. The solution is filtered through a sterile 0.22 micron filter.

It is expected that the above solution should satisfy EP B requirements for preservative efficacy.

The procedure for preparing solution 3D is as follows:
1. To a 250 ml beaker 0.90 grams of Sodium Citrate Dihydrate is added to 95 grams of Purified Water USP. The solution is mixed until the Sodium Citrate Dihydrate dissolved.
2. To the solution of Step 1 are added 0.02 grams of Glycine and 0.01 grams of Ascorbic acid. The solution is mixed until the Glycine and Ascorbic acid dissolved.

3. An additional 4.07 grams of water is added and mixed until the solution is uniform.
4. In a separate a container, 2.0 grams of Hypromellose E4M 2910 is slowly added to 800 g of water at a temperature of 80° C. to 85° C. while mixing. When the addition is completed, the solution is mixed for an additional 30 minutes at a temperature of 80° C. to 85° C. until all of the Hypromellose E4M 2910 is completely dissolved.
5. Heat is removed from the solution of step 4 and the solution is allowed to cool to ambient temperature (20° C. to 30° C.) while mixing.
6. To the solution of Step 5 are added 11.2 grams of Polyethylene Glycol 400 and 2.5 grams of Glycerin while mixing to dissolve.
7. To the solution of Step 6 is added 1.0 grams of the solution of Step 3 while mixing to dissolve.
8. To the solution of Step 7 are added the following ingredients while mixing, allowing time for each to dissolve completely before adding the next: 0.13 grams of Magnesium Chloride, 1.80 grams of Potassium Chloride, 0.04 grams of Glucose and 0.56 grams of Sodium Lactate.
9. To the solution of Step 8, 5.2 grams of Boric acid is slowly added while mixing and mixed until completely dissolved.
10. To the solution of Step 9, are added the following ingredients while mixing, allowing time for each to dissolve completely before adding the next: 0.60 grams of Sodium Borate, and 0.09 grams of a 33% solution of Polyquaternium 42 in water.
11. On completion of addition of all ingredients, additional water is added to bring the weight of the solution to a total of 1,000.00 grams and the solution is mixed for an additional 10 minutes.
12. The solution is filtered through a sterile 0.22 micron filter.

It is expected that the filtered solution should satisfy EP B requirements for preservative efficacy.

The procedure for preparing solution 3E is as follows:
1. To a 250 ml beaker 0.90 grams of Sodium Citrate Dihydrate is added to 95 grams of Purified Water USP. The solution is mixed until the Sodium Citrate Dihydrate dissolved.
2. To the solution of Step 1 is added 0.02 grams of Glycine and 0.01 grams of Ascorbic acid. The solution is mixed until the Glycine and Ascorbic acid dissolved.
3. An additional 4.07 grams of water is added and mixed until the solution is uniform.
4. In a separate a container, 11.2 grams of Polyethylene Glycol 400 and 3.0 grams of Propylene Glycol are slowly added to 930 g of water at a temperature of 20° C. to 30° C. while mixing. The solution is mixed until both ingredients were completely dispersed and dissolved.
5. To the solution of Step 4 is added 1.0 grams of the solution of Step 3 while mixing to dissolve.
6. To the solution of Step 5 are added the following ingredients while mixing, allowing time for each ingredient to dissolve completely before adding the next: 0.27 grams of Disodium Phosphate, 0.13 grams of Magnesium Chloride, 1.80 grams of Potassium Chloride, 0.04 grams of Glucose, and 0.57 grams of Sodium Lactate.
7. To the solution of Step 6, 5.2 grams of Boric acid is slowly added while mixing and mixed until completely dissolved.
8. To the solution of Step 7, are added the following ingredients while mixing, allowing time for each to dissolve completely before adding the next: 0.60 grams of Sodium Borate, 0.25 grams of Naphazoline Hydrochloride, 3.0 grams of Pheniramine Maleate, 3.0 grams of Sodium Chloride and 0.09 grams of a 33% solution of Polyquaternium 42 in water.
9. On completion of addition of all ingredients, additional water is added to bring the weight of the solution to a total of 1,000.00 grams and the solution is mixed for an additional 10 minutes.
10. The solution is filtered through a sterile 0.22 micron filter.

It is expected that the filtered solution should satisfy EP B requirements for preservative efficacy.

TABLE 4

| | Comparative Examples | | | | | |
|---|---|---|---|---|---|---|
| | 4A | | 4B | | 4C | |
| INGREDIENT | % w/w | amount per batch (gms) | % w/w | amount per batch (gms) | % w/w | amount per batch (gms) |
| Tetrahydrozoline Hydrochloride | 0.05 | 0.50 | 0.05 | 0.50 | 0.05 | 0.50 |
| Polyethylene Glycol 400 | — | — | 1.12 | 11.2 | — | — |
| Povidone | — | — | 1.0 | 10.0 | — | — |
| Dextran 70 | — | — | 0.1 | 1.0 | — | — |
| Boric Acid | 1.14 | 11.4 | 1.04 | 10.4 | 0.52 | 5.2 |
| Sodium Borate | 0.09 | 0.9 | 0.09 | 0.9 | 0.06 | 0.6 |
| Disodium Phosphate | — | — | — | — | 0.027 | 0.27 |
| Disodium Edetate | 0.10 | 1.0 | 0.10 | 1.0 | — | — |
| Sodium Citrate | — | — | — | — | 0.0009 | 0.009 |
| Potassium Chloride | — | — | — | — | 0.18 | 1.8 |
| Sodium Chloride | 0.265 | 2.65 | 0.18 | 1.8 | 0.28 | 2.80 |
| 50% Aqueous Solution of Sodium Lactate | — | — | — | — | 0.056 | 0.56 |
| Magnesium Chloride | — | — | — | — | 0.013 | 0.13 |
| Glucose | — | — | — | — | 0.004 | 0.04 |
| Glycine | — | — | — | — | 0.00002 | 0.0002 |

TABLE 4-continued

| | Comparative Examples | | | | | |
|---|---|---|---|---|---|---|
| | 4A | | 4B | | 4C | |
| INGREDIENT | % w/w | amount per batch (gms) | % w/w | amount per batch (gms) | % w/w | amount per batch (gms) |
| Ascorbic Acid | — | — | — | — | 0.00001 | 0.0001 |
| Polyquaternium 42 | 0.004 | 0.040 | 0.004 | 0.040 | 0.003 | 0.030 |
| Purified Water | 98.35 | 983.5 | 96.37 | 963.7 | 98.81 | 988.1 |
| Total | 100.00% | 1000.00 g | 100.00% | 1000.00 g | 100.00% | 1000.00 g |

For Examples 4A-4C

The Tetrahydrozoline Hydrochloride was supplied by PCAS (TURKU, FINLAND). The Polyethylene Glycol 400 was supplied by Clariant Produkte (BURGKIRCHEN, GERMANY). The Povidone was supplied by BASF (LUDWIGSHAFEN, GERMANY). The Dextran 70 was supplied by Pharmacosmos (HOLBAEK, GERMANY). The Boric Acid was supplied by Merck KGaA (DARMSTADT, GERMANY). The Sodium Borate was supplied by Merck KGaA (DARMSTADT, GERMANY). The Disodium Phosphate was supplied by KGaA (DARMSTADT, GERMANY). The Sodium Citrate was supplied by Merck KGaA (DARMSTADT, GERMANY). The Potassium Chloride was supplied by Merck KGaA (DARMSTADT, GERMANY). The Sodium Chloride was supplied by Caldic (DUSSELDORF, GERMANY). The Sodium Lactate was supplied as Sodium Lactate (50% aqueous) by Merck KGaA (DARMSTADT, GERMANY). The Magnesium Chloride was supplied by Merck KGaA (DARMSTADT, GERMANY). The Glucose was supplied by Roquette Freres (LASTREM, FRANCE). The Glycine was supplied by Merck KGaA (DARMSTADT, GERMANY). The Ascorbic Acid was supplied by DSM NUTRITIONAL Products (DRAKEMYRE, SCOTLAND, UK). The Polyquaternium 42 was supplied as Polyquaternium 42 (33% aqueous) by DSM BIOMEDICAL, (BERKELEY, Calif.).

The procedure for preparing solution 4A was as follows:
1. In a suitable sized container, was added 11.4 grams of Boric acid to 950 grams of Purified Water allowing time to mix and dissolve.
2. To the solution of Step 2 were added 1.0 grams of Edetate Disodium and 0.9 gram of Sodium Borate allowing time for each to mix and completely dissolve.
3. To the solution of Step 2 was added 0.50 grams of Tetrahydrozoline Hydrochloride, 2.65 grams of Sodium Chloride and 0.12 grams of a 33% solution of Polyquaternium 42 in water.
4. On completion of addition of all ingredients, additional water is added to bring the weight of the solution to a total of 1,000.00 grams and the solution is mixed for an additional 10 minutes.
5. The solution is filtered through a sterile 0.22 micron filter.

The procedure for preparing solution 4B was as follows:
1. In a suitable sized container, was slowly added 10.0 grams of Povidone to 950 grams of Purified Water while continuing to mix. The solution is mixed to completely dissolve Povidone.
2. To the solution of Step 1 was added 11.2 grams of Polyethylene Glycol 400 and 1.0 gram of Dextran 70 allowing time for each to mix and completely dissolve.
3. To the solution of Step 2 was added 10.4 grams of Boric acid while mixing and the solution was mixed until dissolved.
4. To the solution of Step 3 were added 1.0 gram of Edetate Disodium and 0.9 gram of Sodium Borate allowing time for each to dissolve completely.
5. To the solution in Step 4 were added 0.5 grams of Tetrahydrozoline Hydrochloride, 1.8 grams of Sodium Chloride and 0.12 grams of a 33% solution of Polyquaternium 42 in water.
6. On completion of addition of all ingredients, additional water is added to bring the weight of the solution to a total of 1,000.00 grams and the solution is mixed for an additional 10 minutes.
7. The solution is filtered through a sterile 0.22 micron filter.

The procedure for preparing solution 4C was as follows:
1. To a 250 ml beaker 0.90 grams of Sodium Citrate Dihydrate was added to 95 grams of Purified Water USP. The solution was mixed until the Sodium Citrate Dihydrate dissolved.
2. To the above were added 0.02 grams of Glycine and 0.01 grams of Ascorbic acid. The solution was mixed until the Glycine and Ascorbic acid dissolved.
3. An additional 4.07 grams of water was added and mixed until the solution was uniform.
4. In a separate a container, 1.0 gram of the solution of Step 2 is slowly added to 930 g of water at a temperature of 20° C. to 30° C. while mixing.
5. To the solution of Step 4 were added the following ingredients while mixing, allowing time for each to dissolve completely before adding the next: 0.27 grams of Disodium Phosphate, 0.13 grams of Magnesium Chloride, 1.80 grams of Potassium Chloride, 0.04 grams of Glucose, 0.56 grams of Sodium Lactate.
6. To the solution of Step 5, 5.2 grams of Boric acid was slowly added while mixing and mixed until completely dissolved.
7. To the solution of Step 6, were added the following ingredients while mixing, allowing time for each to dissolve completely before adding the next: 0.60 grams of Sodium Borate, 0.50 grams of Tetrahydrozoline Hydrochloride, 2.8 grams of Sodium Chloride and 0.09 grams of a 33% solution of Polyquaternium 42 in water.
8. On completion of addition of all ingredients, additional water is added to bring the weight of the solution to a total of 1,000.00 grams and the solution is mixed for an additional 10 minutes.
9. The solution is filtered through a sterile 0.22 micron filter.

TABLE 5

Comparative Examples

| INGREDIENT | 5A % w/w | 5A amount per batch (gms) | 5B % w/w | 5B amount per batch (gms) | 5C % w/w | 5C amount per batch (gms) |
|---|---|---|---|---|---|---|
| Tetrahydrozoline Hydrochloride | 0.05 | 0.50 | 0.05 | 0.50 | 0.05 | 0.50 |
| Polyethylene Glycol 400 | 1.13 | 11.3 | 1.00 | 10.0 | 1.13 | 11.3 |
| Glycerin | — | — | — | — | 0.250 | 2.50 |
| Hypromellose E4M 2910 | — | — | — | — | 0.354 | 3.54 |
| Propylene Glycol | — | — | 0.3 | 3.0 | — | — |
| Povidone | 1.0 | 10.0 | — | — | — | — |
| Dextran 70 | 0.1 | 1.0 | 0.1 | 1.0 | — | — |
| Boric Acid | 0.60 | 6.0 | 0.52 | 5.2 | — | — |
| Sodium Borate | 0.095 | 0.95 | 0.090 | 0.90 | 0.15 | 1.50 |
| Disodium Phosphate | — | — | 0.027 | 0.27 | 0.027 | 0.27 |
| Disodium Edetate | 0.10 | 1.0 | 0.10 | 1.0 | 0.10 | 1.0 |
| Sodium Citrate | — | — | 0.0009 | 0.009 | 0.500 | 5.00 |
| Zinc Chloride | 0.010 | 0.10 | 0.010 | 0.10 | — | — |
| Zinc Sulfate Heptahydrate | — | — | — | — | 0.246 | 2.46 |
| Potassium Chloride | — | — | 0.18 | 1.80 | 0.18 | 1.80 |
| Sodium Chloride | 0.300 | 3.00 | — | — | 0.12 | 1.20 |
| 50% Aqueous Solution of Sodium Lactate | — | — | 0.056 | 0.56 | 0.056 | 0.56 |
| Magnesium Chloride | — | — | 0.013 | 0.13 | 0.013 | 0.13 |
| Glucose | — | — | 0.004 | 0.04 | 0.004 | 0.04 |
| Glycine | — | — | 0.00002 | 0.0002 | 0.00002 | 0.0002 |
| Ascorbic Acid | 0.010 | 0.10 | 0.00001 | 0.0001 | 0.00001 | 0.0001 |
| Polyquaternium 42 | 0.005 | 0.050 | 0.003 | 0.030 | 0.003 | 0.030 |
| Purified Water | 96.60 | 966.0 | 96.8 | 968.0 | 96.8 | 968.0 |
| Total | 100.00% | 1000.0 g | 100.00% | 1000.0 g | 100.00% | 1000.0 g |

For Example 5A-5C

The Tetrahydrozoline Hydrochloride can be supplied by PCAS (TURKU, FINLAND). The Polyethylene Glycol 400 can be supplied by Clariant Produkte (BURGKIRCHEN, GERMANY). The Povidone can be supplied by BASF (LUDWIGSHAFEN, GERMANY). The Dextran 70 can be supplied by Pharmacosmos (HOLBAEK, GERMANY). The Boric Acid can be supplied by Merck KGaA (DARMSTADT, GERMANY). The Sodium Borate was supplied by Merck KGaA (DARMSTADT, GERMANY). The Disodium Edetate was supplied by Merck SL (BARCELONA, SPAIN). The Zinc Chloride (64% aqueous) was supplied by Magnesium Products Inc (TULSA, Okla., US). The Sodium Chloride was supplied by Caldic (DUSSELDORF, GERMANY). The Ascorbic Acid was supplied by DSM Nutritional Products (DRAKEMYRE, SCOTLAND, UK). The Polyquaternium 42 was supplied as Polyquaternium 42 (33% aqueous) by DSM BIOMEDICAL, (BERKELEY, Calif.).

The procedure for preparing solution 5A was as follows:
1. In a suitable sized container, was slowly added 10.0 grams of Povidone to 950 grams of Purified Water while continuing to mix. The solution is mixed to completely dissolve Povidone.
2. To the solution of Step 1 was added 11.3 grams of Polyethylene Glycol 400 and 1.0 gram of Dextran 70 allowing time for each to mix and completely dissolve.
3. To the solution of Step 2 was added 6.0 grams of Boric acid while mixing and the solution was mixed until dissolved.
4. To the solution of Step 3 were added 1.0 gram of Edetate Disodium and 0.95 gram of Sodium Borate allowing time for each to dissolve completely.
5. To the solution in Step 4 were added 0.5 grams of Tetrahydrozoline Hydrochloride, 3.0 grams of Sodium Chloride, 0.16 grams of Zinc Chloride solution, 0.1 grams of Ascorbic acid and 0.15 grams of a 33% solution of Polyquaternium 42 in water.
6. On completion of addition of all ingredients, additional water is added to bring the weight of the solution to a total of 1,000.00 grams and the solution is mixed for an additional 10 minutes.
7. The solution is filtered through a sterile 0.22 micron filter.

For Example 5B

The Tetrahydrozoline Hydrochloride can be supplied by PCAS (TURKU, FINLAND). The Polyethylene Glycol 400 can be supplied by Clariant Produkte (BURGKIRCHEN, GERMANY). The Propylene Glycol can be supplied by Spectrum Chemicals (USA). The Dextran 70 can be supplied by Pharmacosmos (HOLBAEK, GERMANY). The Boric Acid can be supplied by Merck KGaA (DARMSTADT, GERMANY). The Sodium Borate can be supplied by Merck KGaA (DARMSTADT, GERMANY). The Disodium Phosphate can be supplied by KGaA (DARMSTADT, GERMANY). The Disodium Edetate was supplied by Merck SL (BARCELONA, SPAIN). The Sodium Citrate can be supplied by Merck KGaA (DARMSTADT, GERMANY). The Zinc Chloride (64% aqueous) was supplied by Magnesium Products Inc (TULSA, Okla., US). The Potassium Chloride can be supplied by Merck KGaA (DARMSTADT, GERMANY). The Sodium Lactate can be supplied as Sodium Lactate (50% aqueous) by Merck KGaA (DARMSTADT, GERMANY). The Magnesium Chloride can be supplied by Merck KGaA (DARMSTADT, GERMANY). The Glucose can be supplied by Roquette Freres (LASTREM, FRANCE). The Glycine can be supplied by Merck KGaA (DARMSTADT, GERMANY). The Ascorbic Acid was supplied by DSM Nutritional Products (DRAKEMYRE, SCOTLAND, UK). The Polyquaternium 42 was supplied as Polyquaternium 42 (33% aqueous) by DSM BIOMEDICAL, (BERKELEY, Calif.).

The procedure for preparing solution 5B was as follows:
1. To a 250 ml beaker 0.90 grams of Sodium Citrate Dihydrate was added to 95 grams of Purified Water USP. The solution was mixed until the Sodium Citrate Dihydrate dissolved.
2. To the solution of Step 1 were added 0.02 grams of Glycine and 0.01 grams of Ascorbic acid. The solution was mixed until the Glycine and Ascorbic acid dissolved.
3. An additional 4.07 grams of water was added and mixed until the solution was uniform.
4. In a separate a container, 10.0 grams of Polyethylene Glycol 400 and 3.0 grams of Propylene Glycol were slowly added to 930 g of water at a temperature of 20° C. to 30° C. while mixing. The solution was mixed until both ingredients were completely dispersed and dissolved.
5. To the solution of Step 4 was added 1.0 grams of the solution of Step 3 while mixing to dissolve.
6. To the solution of Step 5 was slowly added 1.0 gram of Dextran 70. The solution was allowed to mix to fully disperse and dissolve Dextran 70.
7. To the solution of Step 6 were added the following ingredients while mixing, allowing time for each to dissolve completely before adding the next: 0.27 grams of Disodium Phosphate, 0.13 grams of Magnesium Chloride, 1.80 grams of Potassium Chloride, 0.04 grams of Glucose, and 0.57 grams of Sodium Lactate.
8. To the solution of Step 7, 5.2 grams of Boric acid was slowly added while mixing and mixed until completely dissolved.
9. To the solution of Step 8, were added the following ingredients while mixing, allowing time for each to dissolve completely before adding the next: 1.0 gram Disodium Edetate, 0.60 grams of Sodium Borate, 0.50 grams of Tetrahydrozoline Hydrochloride, 0.16 grams of Zinc Chloride solution, and 0.09 grams of a 33% solution of Polyquaternium 42 in water.
10. On completion of addition of all ingredients, additional water is added to bring the weight of the solution to a total of 1,000.00 grams and the solution is mixed for an additional 10 minutes.
11. The solution is filtered through a sterile 0.22 micron filter.

For Example 5C

The Tetrahydrozoline Hydrochloride can be supplied by PCAS (TURKU, FINLAND). The Hypromellose E4M can be supplied by Dow Chemical (PLUQUEMINE, La., USA). The Polyethylene Glycol 400 can be supplied by Clariant Produkte (BURGKIRCHEN, GERMANY). The Glycerin can be supplied by Emery Oleochemicals GmbH (DUSSELDORF, GERMANY). The Boric Acid can be supplied by Merck KGaA (DARMSTADT, GERMANY). The Sodium Borate can be supplied by Merck KGaA (DARMSTADT, GERMANY). The Disodium Phosphate can be supplied by Merck KGaA (DARMSTADT, GERMANY). The Disodium Edetate was supplied by Merck SL (BARCELONA, SPAIN). The Sodium Citrate can be supplied by Merck KGaA (DARMSTADT, GERMANY). The Zinc Sulfate Heptahydrate was supplied by Aventor Performance Materials (PHILLIPSBURG, N.J., USA) Magnesium Products Inc (TULSA, Okla., US). The Potassium Chloride can be supplied by Merck KGaA (DARMSTADT, GERMANY). The Sodium Lactate can be supplied as Sodium Lactate (50% aqueous) by Merck KGaA (DARMSTADT, GERMANY). The Magnesium Chloride can be supplied by Merck KGaA (DARMSTADT, GERMANY). The Glucose can be supplied by Roquette Freres (LASTREM, FRANCE). The Glycine can be supplied by Merck KGaA (DARMSTADT, GERMANY). The Ascorbic Acid was supplied by DSM Nutritional Products (DRAKEMYRE, SCOTLAND, UK). The Polyquaternium 42 was supplied as Polyquaternium 42 (33% aqueous) by DSM BIOMEDICAL, (BERKELEY, Calif.).

The procedure for preparing solution 5C is as follows:
1. To a 250 ml beaker is added 95 grams of Purified Water USP.
2. To the solution of Step 1 is added 0.2 grams of Glycine and 0.01 grams of Ascorbic acid. The solution is mixed until the Ascorbic acid dissolved.
3. An additional 4.09 grams of water is added and mixed until the solution is uniform.
4. In a separate a container, 3.54 grams of Hypromellose E4M 2910 is slowly added to 800 g of water at a temperature of 80° C. to 85° C. while mixing. When the addition is completed, the solution is mixed for an additional 30 minutes at a temperature of 80° C. to 85° C. until all of the Hypromellose E4M 2910 is completely dispersed and dissolved.
5. Heat is removed from the solution of step 4 and the solution is allowed to cool to ambient temperature (20° C. to 30° C.) while mixing.
6. To the solution of Step 5 is added 11.3 grams of Polyethylene Glycol 400 and 2.5 grams of Glycerin while mixing to dissolve.
7. To the solution of Step 6 is added 1.0 gram of the solution of Step 3 while mixing to dissolve.
8. To the solution of Step 7 are added the following ingredients while mixing, allowing time for each ingredient to dissolve completely before adding the next: 0.27 grams of Disodium Phosphate, 5.00 grams of Sodium Citrate, 1.0 gram of Edetate Disodium, 0.13 grams of Magnesium Chloride, 0.04 grams of Glucose, 1.80 grams of Potassium Chloride, and 0.57 grams of Sodium Lactate.
9. To the solution of Step 8, 2.46 grams of Zinc Sulfate Heptahydrate is slowly added while mixing and mixed until completely dissolved.
10. To the solution of Step 9, are added the following ingredients while mixing, allowing time for each ingredient to dissolve completely before adding the next: 1.50 grams of Sodium Borate, 0.50 grams of Tetrahydrozoline Hydrochloride, 1.2 grams of Sodium Chloride and 0.09 grams of a 33% solution of Polyquaternium 42 in water.
11. On completion of addition of all ingredients, additional water is added to bring the weight of the solution to a total of 1,000.00 grams and the solution is mixed for an additional 10 minutes.
12. The solution is filtered through a sterile 0.22 micron filter.

TABLE 6

Examples of the Compositions of the Present Invention

| INGREDIENT | 6A Useful for Relief of Eye Irritation | | 6B Useful for Relief of Dry Eye | | 6C Useful as Eye Wash to Remove Eye Irritants | | 6D Useful as Eye Wash to Remove Eye Irritants | | 6E Useful for Relief of Eye Irritation | |
|---|---|---|---|---|---|---|---|---|---|---|
| | % w/w | amount per batch (gms) | % w/w | amount per batch (gms) | % w/w | amount per batch (gms) | % w/w | amount per batch (gms) | % w/w | amount per batch (gms) |
| Tetrahydrozoline Hydrochloride | 0.05 | 0.25 | — | — | — | — | — | — | 0.05 | 0.50 |
| Polyethylene Glycol 400 | — | — | 0.400 | 2.0 | — | — | — | — | — | — |
| Glycerin | 0.50 | 2.5 | 0.25 | 1.25 | — | — | — | — | 0.50 | 5.0 |
| Hypromellose E3 2910 | — | — | 0.20 | 1.0 | — | — | — | — | — | — |
| Boric Acid | 1.00 | 5.0 | 1.00 | 5.0 | 1.00 | 10.0 | 1.00 | 10.0 | 1.00 | 10.0 |
| Sodium Borate | 0.0045 | 0.0225 | 0.0045 | 0.0225 | 0.0045 | 0.045 | 0.0045 | 0.045 | 0.0045 | 0.045 |
| Disodium Phosphate | — | — | — | — | 0.027 | 0.27 | — | — | 0.027 | 0.27 |
| Sodium Citrate Dihydrate | 0.0009 | 0.0045 | 0.0009 | 0.0045 | 0.0009 | 0.009 | 0.0009 | 0.009 | 0.0009 | 0.009 |
| Potassium Chloride | — | — | — | — | 0.179 | 1.79 | — | — | 0.18 | 1.8 |
| Sodium Chloride | 0.140 | 0.70 | 0.140 | 0.70 | 0.12 | 1.2 | 0.12 | 1.2 | — | — |
| 50% Aqueous Solution of Sodium Lactate | 0.057 | 0.285 | 0.057 | 0.285 | 0.057 | 0.57 | 0.057 | 0.57 | 0.056 | 0.56 |
| Magnesium Chloride | — | — | — | — | 0.013 | 0.13 | — | — | 0.013 | 0.13 |
| Glucose | 0.040 | 0.20 | 0.40 | 2.0 | 0.036 | 0.36 | 0.036 | 0.36 | — | — |
| Glycine | 0.00002 | 0.0001 | 0.00002 | 0.0001 | 0.00002 | 0.0002 | 0.0005 | 0.005 | 0.00002 | 0.0002 |
| Ascorbic Acid | 0.00001 | 0.00005 | 0.00001 | 0.00005 | 0.00001 | 0.0001 | 0.00001 | 0.0001 | 0.00001 | 0.0001 |
| Polyquaternium 42 | 0.003 | 0.015 | 0.003 | 0.015 | 0.003 | 0.030 | 0.003 | 0.030 | 0.003 | 0.030 |
| Purified Water | 98.206 | 491.03 | 97.544 | 487.72 | 98.56 | 985.60 | 98.778 | 987.80 | 98.16 | 981.60 |
| total | 100.00% | 500.00 g | 100.00% | 500.00 g | 100.00% | 1000.00 g | 100.00% | 1000.00 g | 100.00% | 1000.00 g |

For Examples 6A-6E

The Tetrahydrozoline Hydrochloride was supplied by PCAS (TURKU, FINLAND). The Polyethylene Glycol 400 was supplied by Clariant Produkte (BURGKIRCHEN, GERMANY). The Glycerin was supplied by Emery Oleochemicals GmbH (DUSSELDORF, GERMANY). The Hypromellose E3 2910 was supplied by DOW CHEMICAL (PLAQUEMINE, La., USA). The Boric Acid was supplied by Merck KGaA (DARMSTADT, GERMANY). The Sodium Borate was supplied by Merck KGaA (DARMSTADT, GERMANY). The Disodium Phosphate was supplied by Merck KGaA (DARMSTADT, GERMANY). The Sodium Citrate was supplied by Merck KGaA (DARMSTADT, GERMANY). The Potassium Chloride was supplied by KGaA (DARMSTADT, GERMANY). The Sodium Chloride was supplied by Caldic (GERMANY). The Sodium Lactate was supplied as Sodium Lactate (50% aqueous) by Merck KGaA (DARMSTADT, GERMANY). The Magnesium Chloride was supplied by KGaA (DARMSTADT, GERMANY). The Glucose was supplied by Roquette Freres (LASTREM, FRANCE). The Glycine was supplied by Merck KGaA (DARMSTADT, GERMANY). The Ascorbic Acid was supplied by DSM NUTRITIONAL Products (DRAKEMYRE, SCOTLAND, UK). The Polyquaternium 42 was supplied as Polyquaternium 42 (33% aqueous) by DSM BIOMEDICAL, (BERKELEY, Calif.).

The procedure for preparing solution 6A was as follows:
1. To a 250 ml beaker 0.90 grams of Sodium Citrate Dihydrate was added to 95 grams of Purified Water USP. The solution was mixed until the Sodium Citrate Dihydrate dissolved.
2. To the above were added 0.02 grams of Glycine and 0.01 grams of Ascorbic acid. The solution was mixed until the Glycine and Ascorbic acid dissolved.
3. An additional 4.07 grams of water was added and mixed until the solution was uniform.
4. In a separate 1500 ml beaker, 1.0 gram of the solution of Step 3 is slowly added to 930 g of water at a temperature of 20° C. to 30° C. while mixing.
5. To the solution of Step 4 were added the following ingredients while mixing, allowing time for each to dissolve completely before adding the next: 0.4 grams of Glucose and 0.0450 grams of Sodium Borate.
6. To the solution of Step 5, 10.0 grams of Boric acid was slowly added while mixing and mixed until completely dissolved.
7. To the solution of Step 6, were added the following ingredients while mixing, allowing time for each to dissolve completely before adding the next, 1.4 grams of Sodium Chloride, 0.57 grams of Sodium Lactate, and 0.09 grams of a 33% solution of Polyquaternium 42 in water.
8. Additional water is added to bring the weight of the solution to a total of 980.00 grams and the solution is mixed for an additional 10 minutes.
9. Into a 1 liter beaker is added 490 grams of the above solution.
10. To the solution in Step 9 is added 2.50 g Glycerin while mixing until completely dispersed and dissolved.
11. To the solution in Step 10 is added 0.25 grams of Tetrahydrozoline HCl and the solution is mixed until completely dissolved.

12. On completion of ingredients, additional water is added to bring the weight of the solution to a total of 500.00 grams and the solution is mixed for an additional 10 minutes.
13. The solution is filtered through a sterile 0.22 micron filter.

The procedure for preparing solution 6B was as follows:
1. To a 250 ml beaker 0.90 grams of Sodium Citrate Dihydrate was added to 95 grams of Purified Water USP. The solution was mixed until the Sodium Citrate Dihydrate dissolved.
2. To the above were added 0.02 grams of Glycine and 0.01 grams of Ascorbic acid. The solution was mixed until the Glycine and Ascorbic acid dissolved.
3. An additional 4.07 grams of water was added and mixed until the solution was uniform.
4. In a separate 1500 ml beaker, 1.0 gram of the solution of Step 3 is slowly added to 930 g of water at a temperature of 20° C. to 30° C. while mixing.
5. To the solution of Step 4 were added the following ingredients while mixing, allowing time for each to dissolve completely before adding the next: 4.0 grams of Glucose and 0.0450 grams of Sodium Borate.
6. To the solution of Step 5, 10.0 grams of Boric acid was slowly added while mixing and mixed until completely dissolved.
7. To the solution of Step 6, were added the following ingredients while mixing, allowing time for each to dissolve completely before adding the next, 1.4 grams of Sodium Chloride, 0.57 grams of Sodium Lactate and 0.09 grams of a 33% solution of Polyquaternium 42 in water.
8. Additional water was added to bring the weight of the solution to a total of 980.00 grams and the solution was mixed for an additional 10 minutes.
9. Into a 1 liter beaker was added 490 grams of the above solution.
10. To the solution of Step 9 was added, 1.0 gram of Hypromellose E3 2910 slowly while mixing. When the addition was completed, the solution was mixed for an additional 30 minutes at ambient temperature until all of the Hypromellose E3 2910 was completely dispersed and dissolved.
11. To the solution of Step 10 was added 1.25 grams of Glycerin while mixing to dissolve.
12. To the solution of Step 11 was added 2.00 grams of Polyethylene Glycol 400 while mixing to dissolve.
13. On completion of ingredients, additional water is added to bring the weight of the solution to a total of 500.00 grams and the solution is mixed for an additional 10 minutes.
14. The solution is filtered through a sterile 0.22 micron filter.

The procedure for preparing solution 6C was as follows:
1. To a 250 ml beaker 0.90 grams of Sodium Citrate Dihydrate was added to 95 grams of Purified Water USP. The solution was mixed until the Sodium Citrate Dihydrate dissolved.
2. To the above were added 0.02 grams of Glycine and 0.01 grams of Ascorbic acid. The solution was mixed until the Glycine and Ascorbic acid dissolved.
3. An additional 4.07 grams of water was added and mixed until the solution was uniform.
4. In a separate 1500 ml beaker, 1.0 gram of the solution of Step 3 is slowly added to 930 g of water at a temperature of 20° C. to 30° C. while mixing.
5. To the solution of Step 4 were added the following ingredients while mixing, allowing time for each to dissolve completely before adding the next: 0.27 grams of Disodium Phosphate, 0.13 grams of Magnesium Chloride, 1.79 grams of Potassium Chloride, 0.36 grams of Glucose, and 0.045 grams of Sodium Borate.
6. To the solution of Step 5 10.0 grams of Boric acid was slowly added while mixing and mixed until completely dissolved
7. To the solution of Step 6, were added the following ingredients while mixing, allowing time for each to dissolve completely before adding the next, 1.4 grams of Sodium Chloride 0.57 grams of Sodium Lactate, and 0.09 grams of a 33% solution of Polyquaternium 42 in water.
8. Additional water was added to bring the weight of the solution to a total of 1,000.00 grams and the solution was mixed for an additional 10 minutes.
9. The solution is filtered through a sterile 0.22 micron filter.

The procedure for preparing solution 6D was as follows:
1. To a 250 ml beaker 0.90 grams of Sodium Citrate Dihydrate was added to 95 grams of Purified Water USP. The solution was mixed until the Sodium Citrate Dihydrate dissolved.
2. To the above were added 0.50 grams of Glycine and 0.01 grams of Ascorbic acid. The solution was mixed until the Glycine and Ascorbic acid dissolved.
3. An additional 3.59 grams of water was added and mixed until the solution was uniform.
4. In a separate 1500 ml beaker, 1 gram of the solution of Step 3 is slowly added to 920 g of water at a temperature of 20° C. to 30° C. while mixing.
5. To the solution of Step 4 were added the following ingredients while mixing, allowing time for each to dissolve completely before adding the next: 0.36 grams of Glucose and 0.045 grams of Sodium Borate.
6. To the solution of Step 5, 10.0 grams of Boric acid was slowly added while mixing and mixed until completely dissolved.
7. To the solution of Step 6, were added the following ingredients while mixing, allowing time for each to dissolve completely before 1.20 grams of Sodium Chloride, 0.57 grams of Sodium Lactate, and 0.090 grams of a 33% solution of Polyquaternium 42 in water.
8. Additional water is added to bring the weight of the solution to a total of 1000.00 grams and the solution is mixed for an additional 10 minutes.
9. The solution is filtered through a sterile 0.22 micron filter.

The procedure for preparing solution 6E was as follows:
1. To a 250 ml beaker 0.90 grams of Sodium Citrate Dihydrate was added to 95 grams of Purified Water USP. The solution was mixed until the Sodium Citrate Dihydrate dissolved.
2. To the above were added 0.02 grams of Glycine and 0.01 grams of Ascorbic acid. The solution was mixed until the Glycine and Ascorbic acid dissolved.
3. An additional 4.07 grams of water were added and mixed until the solution was uniform.
4. Into a separate 1500 ml beaker, 1.0 gram of the solution of Step 3 is slowly added to 930 g of water at a temperature of 20° C. to 30° C. while mixing.
5. To the solution of Step 4 were added the following ingredients while mixing, allowing time for each to dissolve before adding the next: 0.27 g Sodium Phosphate Dibasic, 0.13 g Magnesium Chloride, 1.8 g Potassium Chloride, and 0.0450 grams of Sodium Borate.
6. To the solution of Step 5, 5.0 grams of Glycerin were slowly added while mixing and mixed until completely dissolved.
7. To the solution of Step 6, 10.0 grams of Boric acid were slowly added while mixing and mixed until completely dissolved.
8. To the solution of Step 8, were added the following ingredients while mixing, allowing time for each to dissolve completely before adding the next, 0.56 g Sodium Lactate, 0.50 g Tetrahydrozoline Hydrochloride, and 0.09 grams of a 33% solution of Polyquaternium 42 in water.
9. Additional water was added to bring the weight of the solution to a total of 1,000.00 grams and the solution was mixed for an additional 10 minutes.
10. The solution is filtered through a sterile 0.22 micron filter.

plied by Merck KGaA (DARMSTADT, GERMANY). The Sodium Citrate was supplied by Merck KGaA (DARMSTADT, GERMANY). The Potassium Chloride was supplied by KGaA (DARMSTADT, GERMANY). The Sodium Lactate was supplied as Sodium Lactate (50% aqueous) by Merck KGaA (DARMSTADT, GERMANY). The Magnesium Chloride was supplied by KGaA (DARMSTADT, GERMANY). The Glucose was supplied by Roquette Freres (LASTREM, FRANCE). The Glycine was supplied by Merck KGaA (DARMSTADT, GERMANY). The Ascorbic Acid was supplied by DSM NUTRITIONAL Products (DRAKEMYRE, SCOTLAND, UK). The Polyquaternium 42 was supplied as Polyquaternium 42 (33% aqueous) by DSM BIOMEDICAL, (BERKELEY, Calif.).

The procedure for preparing solution 7A was as follows:
1. To a 250 ml beaker was added to 95 grams of Purified Water USP.
2. To the above were added 0.02 grams of Glycine and 0.01 grams of Ascorbic acid. The solution was mixed until the Glycine and Ascorbic acid dissolved.

TABLE 7

Examples of the Compositions of the Present Invention

| INGREDIENT | 7A Useful for Relief of Dry Eye Irritation | | 7B Useful for Relief of Dry Eye Irritation | | 7C Useful for Relief of Dry Eye Irritation | |
|---|---|---|---|---|---|---|
| | % w/w | amount per batch (gms) | % w/w | amount per batch (gms) | % w/w | amount per batch (gms) |
| Sodium Hyaluronate | 0.20 | 2.0 | — | — | 0.07 | 0.70 |
| Tamarind Seed Polysaccharide | — | — | 0.5 | 5.0 | 0.180 | 1.80 |
| Polyethylene Glycol 400 | 1 | 10.00 | 1 | 10.00 | 0.40 | 4.0 |
| Glycerin | 0.25 | 2.5 | 0.25 | 2.5 | 0.10 | 1.0 |
| Hypromellose E3 2910 | 0.20 | 2.0 | 0.20 | 2.0 | 0.07 | 0.7 |
| Boric Acid | 0.80 | 8.0 | 0.80 | 8.0 | 0.80 | 8.0 |
| Disodium Phosphate | 0.027 | 0.27 | 0.027 | 0.27 | 0.027 | 0.27 |
| Sodium Citrate Dihydrate | 0.28 | 2.8 | 0.25 | 2.5 | 0.18 | 1.8 |
| Potassium Chloride | 0.18 | 1.8 | 0.18 | 1.8 | 0.18 | 1.8 |
| 50% Aqueous Solution of Sodium Lactate | 0.057 | 0.57 | 0.057 | 0.57 | 0.057 | 0.57 |
| Magnesium Chloride | 0.013 | 0.13 | 0.013 | 0.13 | 0.013 | 0.13 |
| Glucose | 0.0036 | 0.036 | 0.0036 | 0.036 | 0.0036 | 0.036 |
| Glycine | 0.00002 | 0.0002 | 0.00002 | 0.0002 | 0.00002 | 0.0002 |
| Ascorbic Acid | 0.00001 | 0.0001 | 0.00001 | 0.0001 | 0.00001 | 0.0001 |
| Polyquaternium 42 | 0.003 | 0.030 | 0.003 | 0.030 | 0.003 | 0.030 |
| Purified Water | 96.986 | 969.90 | 96.716 | 967.20 | 97.916 | 979.20 |
| total | 100.00% | 1000.00 g | 100.00% | 1000.00 g | 100.00% | 1000.00 g |

For Examples 7A-7C

The Sodium Hyaluronate was supplied by LIFECORE (CHASKA, Minn., US). The Tamarind Seed Polysaccharide was supplied by FARMIGEA (OSPEDALETTO, ITALY). The Polyethylene Glycol 400 was supplied by Clariant Produkte (BURGKIRCHEN, GERMANY). The Glycerin was supplied by Emery Oleochemicals GmbH (DUSSELDORF, GERMANY). The Hypromellose E3 2910 was supplied by DOW CHEMICAL (PLAQUEMINE, La., USA). The Boric Acid was supplied by Merck KGaA (DARMSTADT, GERMANY). The Disodium Phosphate was sup- 3. An additional 4.97 grams of water were added and mixed until the solution was uniform.
4. In a separate 1000 ml beaker, 2.0 gram of Hypromellose E3 2910 was slowly added to 600 g of water at a temperature of 20° C. to 30° C. while mixing. When the addition was completed, the solution was mixed for an additional 30 minutes at ambient temperature until all of the Hypromellose E3 2910 was completely dispersed and dissolved.
5. To the solution of Step 4, 1.0 gram of the solution of Step 3 was slowly added and mixed to disperse and dissolve.

6. To the solution of Step 5 were added the following ingredients while mixing, allowing time for each to dissolve completely before adding the next: 0.27 grams of Disodium Phosphate, 0.13 grams of Magnesium Chloride, 1.8 grams of Potassium Chloride, and 0.036 grams of Glucose.
7. To the solution of Step 6, 2.5 grams of Glycerin and 10.0 grams of Polyethylene Glycol 400 were slowly added while mixing, allowing for each to completely dissolve before the next addition.
8. To the solution of Step 7, 8.0 grams of Boric acid were slowly added while mixing and mixed until completely dissolved.
9. To the solution of Step 8, were added the following ingredients while mixing, allowing time for each to dissolve completely before adding the next, 0.57 grams of Sodium Lactate, and 0.09 grams of a 33% solution of Polyquaternium 42 in water.
10. Additional water was added to bring the weight of the solution to a total of 660.00 grams and the solution was mixed for an additional 10 minutes.
11. To a separate 1500 ml beaker was added 990.0 g of water.
12. To the solution of step 11 were slowly added 6.0 g Sodium Hyaluronate while mixing vigorously at a temperature of 20° C. to 30° C. to create a vortex.
13. The above solution was mixed until completely dispersed.
14. Sufficient water was added to bring the weight of the solution of Step 13 to 1,000.00 grams and the solution was mixed for an additional 10 minutes.
15. To the solution of Step 10 was slowly added 333.00 grams of the solution of Step 14 while mixing vigorously at a temperature of 20° C. to 30° C. to create a vortex.
16. To the solution of Step 15 was slowly added 2.80 grams of Sodium Citrate while mixing to completely disperse and dissolve.
17. Additional water was added to bring the weight of the solution to a total of 1,000.00 grams and the solution was mixed for an additional 10 minutes.
18. The solution is filtered through a sterile 0.22 micron filter.

The procedure for preparing solution 7B was as follows:
1. To a 250 ml beaker was added to 95 grams of Purified Water USP.
2. To the above were added 0.02 grams of Glycine and 0.01 grams of Ascorbic acid. The solution was mixed until the Glycine and Ascorbic acid dissolved.
3. An additional 4.97 grams of water were added and mixed until the solution was uniform.
4. In a separate 1000 ml beaker, 2.0 gram of Hypromellose E3 2910 was slowly added to 600 g of water at a temperature of 20° C. to 30° C. while mixing. When the addition was completed, the solution was mixed for an additional 30 minutes at ambient temperature until all of the Hypromellose E3 2910 was completely dispersed and dissolved.
5. To the solution of Step 4, 1.0 gram of the solution of Step 3 was slowly added and mixed to disperse and dissolve.
6. To the solution of Step 5 were added the following ingredients while mixing, allowing time for each to dissolve completely before adding the next: 0.27 grams of Disodium Phosphate, 0.13 grams of Magnesium Chloride, 1.8 grams of Potassium Chloride, and 0.036 grams of Glucose.
7. To the solution of Step 6, 2.5 grams of Glycerin and 10.0 grams of Polyethylene Glycol 400 were slowly added while mixing, allowing for each to completely dissolve before the next addition.
8. To the solution of Step 7, 8.0 grams of Boric acid were slowly added while mixing and mixed until completely dissolved.
9. To the solution of Step 8, were added the following ingredients while mixing, allowing time for each to dissolve completely before adding the next, 0.57 grams of Sodium Lactate, and 0.09 grams of a 33% solution of Polyquaternium 42 in water.
10. Additional water was added to bring the weight of the solution to a total of 660.00 grams and the solution was mixed for an additional 10 minutes.
11. To a separate 1000 ml beaker was added 450.0 g of water.
12. To the solution of step 11 were slowly added 7.5 g Tamarind Seed Polysaccharide while mixing vigorously at a temperature of 20° C. to 30° C. to create a vortex.
13. The above solution was mixed until completely dispersed.
14. Sufficient water was added to bring the weight of the solution of Step 13 to 500.00 grams and the solution was mixed for an additional 10 minutes.
15. To the solution of Step 10 was slowly added 333.00 grams of the solution of Step 14 while mixing vigorously at a temperature of 20° C. to 30° C. to create a vortex.
16. To the solution of Step 15 was slowly added 2.50 grams of Sodium Citrate while mixing to completely disperse and dissolve.
17. Additional water was added to bring the weight of the solution to a total of 1,000.00 grams and the solution was mixed for an additional 10 minutes.
18. The solution is filtered through a sterile 0.22 micron filter.

The procedure for preparing solution 7C was as follows:
1. To a 250 ml beaker was added to 95 grams of Purified Water USP.
2. To the above were added 0.02 grams of Glycine and 0.01 grams of Ascorbic acid. The solution was mixed until the Glycine and Ascorbic acid dissolved.
3. An additional 4.97 grams of water were added and mixed until the solution was uniform.
4. In a separate 1000 ml beaker, 0.7 gram of Hypromellose E3 2910 was slowly added to 600 g of water at a temperature of 20° C. to 30° C. while mixing. When the addition was completed, the solution was mixed for an additional 30 minutes at ambient temperature until all of the Hypromellose E3 2910 was completely dispersed and dissolved.
5. To the solution of Step 4, 1.0 gram of the solution of Step 3 was slowly added and mixed to disperse and dissolve.
6. To the solution of Step 5 were added the following ingredients while mixing, allowing time for each to dissolve completely before adding the next: 0.27 grams of Disodium Phosphate, 0.13 grams of Magnesium Chloride, 1.8 grams of Potassium Chloride, and 0.036 grams of Glucose.
7. To the solution of Step 6, 1.0 gram of Glycerin and 4.0 grams of Polyethylene Glycol 400 were slowly added while mixing, allowing for each to completely dissolve before the next addition.

8. To the solution of Step 7, 8.0 grams of Boric acid were slowly added while mixing and mixed until completely dissolved.
9. To the solution of Step 8, were added the following ingredients while mixing, allowing time for each to dissolve completely before adding the next, 0.57 grams of Sodium Lactate, and 0.09 grams of a 33% solution of Polyquaternium 42 in water.
10. Additional water was added to bring the weight of the solution to a total of 660.00 grams and the solution was mixed for an additional 10 minutes.
11. To a separate 1500 ml beaker was added 990.0 g of water.
12. To the solution of step 11 were slowly added 2.1 g of Sodium Hyaluronate while mixing vigorously at a temperature of 20° C. to 30° C. to create a vortex.
13. The above solution was mixed until completely dispersed.
14. To the above were added 5.4 g of Tamarind Seed Polysaccharide while mixing vigorously at a temperature of 20° C. to 30° C. to create a vortex and the solution was mixed to completely disperse.
15. Sufficient water was added to bring the weight of the solution of Step 14 to 1000.00 grams and the solution was mixed for an additional 10 minutes.
16. To the solution of Step 10 was slowly added 333.00 grams of the solution of Step 14 while mixing vigorously at a temperature of 20° C. to 30° C. to create a vortex.
17. To the solution of Step 16 was slowly added 1.80 grams of Sodium Citrate while mixing to completely disperse and dissolve.
18. Additional water was added to bring the weight of the solution to a total of 1,000.00 grams and the solution was mixed for an additional 10 minutes.
19. The solution is filtered through a sterile 0.22 micron filter.

The formulations of Examples 1A-1D, 2A-2B, 4A-4C and 5A-5C were tested for preservative efficacy using the EP B Criteria described above. Table 8 summarizes the results of this preservative testing.

TABLE 8

Preservative Efficacy Results

| Example | Polyquaternium Compound | Polyol Compound | Borate | Antimicrobial Mixture | Zn | Results of EP B Criteria Test | Log Reduction of fungal microorganism* |
|---|---|---|---|---|---|---|---|
| 1A | Present | Present | Present | Present | Absent | Criteria Satisfied | 2.1 |
| 1B | Present | Present | Present | Present | Absent | Criteria Satisfied | 2.5 |
| 1C | Present | Present | Present | Present | Absent | Criteria Satisfied | 1.3 |
| 1D | Present | Present | Present | Present | Absent | Criteria Satisfied | 1.8 |
| 2A | Present | Present | Present | Present | Absent | Criteria Satisfied | 1.3 |
| 2B | Present | Present | Present | Present | Absent | Criteria Satisfied | 1.4 |
| 4A | Present | Absent | Present | Absent | Absent | Failed Criteria | 0.3 |
| 4B | Present | Present | Present | Absent | Absent | Failed Criteria | 0.2 |
| 4C | Present | Absent | Present | Present | Absent | Failed Criteria | 0.9 |
| 5A | Present | Present | Present | Absent | Present | Failed Criteria | 0.9 |
| 5B | Present | Present | Present | Present | Present | Failed Criteria | 0.2 |
| 5C | Present | Present | Present | Present | Present | Failed Criteria | 1.2 |
| 6A | Present | Present | Present | Partial** | Absent | Criteria Satisfied | 3.2 |
| 6B | Present | Present | Present | Partial** | Absent | Criteria Satisfied | 2.9 |
| 6C | Present | Absent | Present | Present | Absent | Criteria Satisfied | 3.8 |
| 6D | Present | Absent | Present | Partial** | Absent | Criteria Satisfied | 4.1 |
| 6E | Present | Present | Present | Partial*** | Absent | Failed Criteria | 0.5 |
| 7A | Present | Present | Present | Present | Absent | Criteria Satisfied | 4.0 |
| 7B | Present | Present | Present | Present | Absent | Criteria Satisfied | 4.0 |
| 7C | Present | Present | Present | Present | Absent | Criteria Satisfied | 4.0 |

*As determined using the EP B Criteria and determining cell count by plated count.
**Formulation contains only certain nutrients of the antimicrobial mixture (i.e., they contain a citrate, a lactate, glucose, glycine, and ascorbic acid)
***Formulation contains only certain nutrients of the antimicrobial mixture, but without glucose (i.e., they contain a citrate, a lactate, glycine, and ascorbic acid)

Observations:

Based on the preservative efficacy testing, each of the compositions Examples 1A-1D and 2A-2B which contain the polyquaternium compound, polyol, borate and antimicrobial mixture as described in the present specification satisfied the criteria of the EP B Criteria preservative efficacy test.

Each of the compositions of Examples 4A (missing the polyol and nutrient component of the antimicrobial mixture), 4B (missing nutrient component of the antimicrobial mixture), 4C (missing the polyol) and 5A (missing nutrient component of the antimicrobial mixture) failed the criteria of the criteria of the EP B Criteria preservative efficacy test.

Although each of the compositions of Examples 5B 5C contain a polyquaternium compound, a polyol, a borate and the electrolyte and nutrient components of the antimicrobial mixture, they failed the criteria of the criteria of the EP B Criteria preservative efficacy test (see Results of EP B Criteria Test for Examples 5B and 5C).

Examples 5A-5C, however, also contain zinc ions. Notably, all of Examples 5A-5C containing zinc ions failed the criteria of the criteria of the EP B Criteria preservative efficacy test suggesting zinc ions may negatively affect the antimicrobial activity of the inventive composition as disclosed herein. In this instance, such zinc containing compositions did not meet EP B Criteria for reducing gram negative bacteria.

In addition to satisfying the criteria of the EP B Criteria preservative efficacy test, Examples 1A-1B also showed fungicidal effect of greater than 2 log reductions of viable cell count of fungi.

Examples 6A, 6C, and 6D how that the pharmaceutically active compounds the criteria of the EP B Criteria preservative efficacy test is satisfied by the compositions of the present invention without the presence of a polyol and with only certain of the nutrients of the antimicrobial mixture.

A comparison of Examples 1B (tetrahydrozoline+ polyol=test satisfied), 4C (tetrahydrozoline+no polyol=test not satisfied) and 6C (no polyol+no tetrahydrozoline=test satisfied) shows that the presence of the pharmaceutically active compound tetrahydrozoline further requires the presence of a polyol for satisfying the criteria of the EP B Criteria preservative efficacy test.

Embodiments of the Present Invention

1. A composition, comprising:
a) from about 0.0005% w/v (weight to volume) to about 0.1000% w/v, of the total composition, of a polyquaternium compound;
b) optionally, from about 0.2% w/v to about 2.0% w/v, of the total composition, of an amount of a polyol or combination polyols;
c) from about 0.02% w/v to about 1.5% w/v, of the total composition, of a borate; and
d) an antimicrobial mixture comprising:
   i. one or more nutrients; and
   ii. optionally, one or more electrolytes
such that:
   a. the total nutrient concentration, in the total composition, is from about 1.0 mMol/L to about 4.0 mMol/L of the composition; and
   b. when present, the total electrolyte concentration, in the total composition, is from about 20.0 mMol/L to about 80.0 mMol/L of the composition.

2 The composition of embodiment 1 wherein the polyquaternium compound has a weight average molecular weight of from about 150 to about 15,000 Daltons.

3. The composition of embodiments 1 and/or 2, wherein the polyquaternium compound has a weight average molecular weight of from about 200 to about 13,500 Daltons 4. The composition of any one, or a combination, of the preceding embodiments, wherein the polyquaternium compound has a weight average molecular weight of from about about 250 to about 12,000 Daltons.

5. The composition of any one, or a combination, of the preceding embodiments, wherein the composition comprises from about 0.0010% w/v to about 0.0200% w/v, of the total composition, of the polyquaternium compound.

6. The composition of any one, or a combination, of the preceding embodiments, wherein the composition comprises from about 0.0010% w/v to about 0.0050% w/v, of the total composition, of the polyquaternium compound.

7. The composition of any one, or a combination, of the preceding embodiments, wherein the polyquaternium compound is selected from the group consisting of polyquaternium-1, polyquaternium-10, polyquaternium-42 or mixtures.

8. The composition of any one, or a combination, of the preceding embodiments, wherein the polyquaternium compound is polyquaternium-42.

9. The composition of any one, or a combination, of the preceding embodiments, wherein the composition comprises from about 0.2% w/v to about 1.7% w/v, of the total composition, of the polyol.

10. The composition of any one, or a combination, of the preceding embodiments, wherein the composition comprises from about 0.4% w/v to about 1.5% w/v, of the total composition, of the polyol.

11. The composition of any one, or a combination, of the preceding embodiments, wherein the polyol is selected from the group consisting of sugars, sugar alcohols, sugar acids, uronic acids and mixtures thereof.

12. The composition of any one, or a combination, of the preceding embodiments, wherein the polyol is selected from the group consisting of sugars, sugar alcohols, sugar acids and mixtures thereof.

13. The composition of any one, or a combination, of the preceding embodiments, wherein the polyol is selected from the group consisting of mannitol, glycerin, polysorbate 80, propylene glycol, polyethylene glycol, sorbitol and mixtures thereof. 14. The composition of any one, or a combination, of the preceding embodiments, wherein the composition comprises from about 0.04% w/v to about 1.0% w/v, of the total composition, of the borate.

15. The composition of any one, or a combination, of the preceding embodiments, wherein the composition comprises from about 0.06% w/v to about 0.60% w/v, of the total composition, of the borate.

16. The composition of any one, or a combination, of the preceding embodiments, wherein the borate is selected from the group consisting of sodium borate, potassium borate, calcium borate, magnesium borate, manganese borate; and mixtures thereof.

17. The composition of any one, or a combination, of the preceding embodiments, wherein the total nutrient concentration, in the total composition, is from about 2.0 mMol/L to about 3.0 mMol/L of the composition.

18. The composition of any one, or a combination, of the preceding embodiments, wherein the total nutrient concentration, in the total composition, is from about 2.8 mMol/L to about 3.0 mMol/L of the composition.

19. The composition of any one, or a combination, of the preceding embodiments, wherein the total nutrient concentration of the composition comprises one or more of:
   a. lactate at a concentration of from about 0 mMol/L to about 10.0 mMol/L of the total composition;
   b. citrate at a concentration of from about 0 mMol/L to about 0.5 mMol/L of the total composition;
   c. phosphate at a concentration of from about 0 mMol/L to about 10 mMol/L of the total composition
   d. glucose at a concentration of from about 0.1 mMol/L to about 25 mMol/L of the total composition;
   e. ascorbic acid at a concentration of from about 0.0003 mMol/L to about 0.0010 mMol/L of the total composition.

20. The composition of any one, or a combination, of the preceding embodiments, wherein the total electrolyte concentration, in the total composition, is from about 30 mMol/L to about 70 mMol/L of the total composition.

21. The composition of any one, or a combination, of the preceding embodiments, wherein the total electrolyte concentration, in the total composition, is from about 40 mMol/L to about 60 mMol/L of the composition.

22. The composition of any one, or a combination, of the preceding embodiments, wherein the total electrolyte concentration comprises one or more of:
   a. potassium at a concentration of from about 24 mMol/L to about 28 mMol/L of the total composition;
   b. sodium at a concentration of from about 5 mMol/L to about 10 mMol/L of the total composition;
   c. magnesium at a concentration of from about 0.50 mMol/L to about 0.80 mMol/L of the total composition; and
   d. chloride at a concentration of from about 23 mMol/L to about 28 mMol/L of the total composition.

23. A method for treating or preventing dry eye comprising the step of applying the composition of embodiment 1 to a subject in need of such treatment or prevention.

24. A method for treating or preventing minor eye irritation comprising the step of applying the composition of embodiment 1 to a subject in need of such treatment or prevention.

25. A method for treating or preventing eye allergy comprising the step of applying the composition of embodiment 1 to a subject in need of such treatment or prevention.

26. A method for improving overall preservative efficacy of a liquid composition, comprising the step of combining:
   a) from about 0.0005% w/v (weight to volume) to about 0.1000% w/v, of the total composition, of a polyquaternium compound;
   b) optionally, from about 0.2% w/v to about 2.0% w/v, of the total composition, of an amount of a polyol or combination polyols;
   c) from about 0.02% w/v to about 1.5% w/v, of the total composition, of a borate; and
   d) an antimicrobial mixture comprising:
      i. one or more nutrients; and
      ii. optionally, one or more electrolytes
   such that:
      a. the total nutrient concentration, in the total composition, is from about 1.0 mMol/L to about 4.0 mMol/L of the composition; and
      b. when present, the total electrolyte concentration, in the total composition, is from about 20.0 mMol/L to about 80.0 mMol/L of the composition.

27. The method of embodiment 26, wherein the preservative efficacy of the liquid composition satisfies the criteria of the EP B Criteria described in the Specification.

28. The method of embodiment 26 and/or 27, wherein the liquid composition is an aqueous liquid preparation.

29. A method for improving antifungal activity of a liquid composition, comprising the step of combining:
   a) from about 0.0005% w/v (weight to volume) to about 0.1000% w/v, of the total composition, of a polyquaternium compound;
   b) optionally, from about 0.2% w/v to about 2.0% w/v, of the total composition, of an amount of a polyol or combination polyols;
   c) from about 0.02% w/v to about 1.5% w/v, of the total composition, of a borate; and
   d) an antimicrobial mixture comprising:
      i. one or more nutrients; and
      ii. optionally, one or more electrolytes
   such that:
      a. the total nutrient concentration, in the total composition, is from about 1.0 mMol/L to about 4.0 mMol/L of the composition; and
      b. when present, the total electrolyte concentration, in the total composition, is from about 20.0 mMol/L to about 80.0 mMol/L of the composition.

30. The method of embodiment 29, wherein, when tested accordance with the EP B Critera described in the Specification, the liquid composition provides fungicidal effect of greater than or equal to 1 log reduction of viable cell count of fungi 14 days after inoculation of the composition with the fungi.

31. The method of embodiment 29 and/or 30, wherein, when tested accordance with the EP B Critera described in the Specification, the liquid composition provides fungicidal effect of greater than or equal to about 2 log reduction of viable cell count of fungi 14 days after inoculation of the composition with the fungi.

32. A composition comprising the following formulation:
   a. from about 0.01% w/v (weight to volume) to about 0.2% w/v vasoconstictor;
   b. from about 0.0015% w/v to about 0.0036% w/v polyquaternium 42;
   c. from about 0.2% w/v to about 1.2% w/v polyethylene glycol 400;
   d. from about 0.2% w/v to about 1.3% w/v glycerin;
   e. from about 0.004% w/v to about 0.6% w/v borate;
   f. from about 0.05% w/v to about 0.2% w/v lactate or pharmaceutically acceptable salt thereof;
   g. from about 0.003% w/v to about 0.4% w/v, optionally 0.003% to about 0.04% w/v glucose;
   h. from about 0% w/v to about 2.5% w/v hypromellose; and
   i. water.

33. The composition of embodiment 32 wherein the pharmaceutically active compound is selected from glaucoma therapeutics, pain relievers, anti-inflammatory, vasoconstrictors, dry eye relievers and anti-allergy medications, anti-infectives or mixtures thereof.

34. A composition, comprising:
   a) from about 0.0005% w/v (weight to volume) to about 0.1000% w/v, of the total composition, of a polyquaternium compound; and
   b) from about 0.002% w/v to about 1% w/v, of saccharide selected from monosaccharide, disaccharide, isomers thereof or mixtures thereof.

35. The composition of embodiment 34 wherein the saccharide is a monosaccharide.

36. A method for preventing the growth of or reducing the number of viable fungal organisms in an environment or medium, comprising the steps of;

a.) preparing a composition comprising:
  i) from about 0.0005% w/v (weight to volume) to about 0.1000% w/v, of the total composition, of a polyquaternium compound; and
  ii) from about 0.002% w/v to about 1% w/v, of saccharide selected from monosaccharide, disaccharide, isomers thereof or mixtures thereof; and
b.) administering (or adding) the composition to the environment or medium.

37. The method of embodiment 36, wherein the fungal organism is mold.

38. The method of embodiment 36 and/or 37 wherein the saccharide is a monosaccharide.

What is claimed is:

1. A composition, comprising a formulation selected from:

| INGREDIENT | A % w/w | B % w/w | C % w/w | D % w/w |
|---|---|---|---|---|
| Tetrahydrozoline Hydrochloride | About 0.05 | About 0.05 | About 0.05 | — |
| Polyethylene Glycol 400 | — | About 1.12 | About 1.12 | About 1.12 |
| Glycerin | About 0.50 | About 0.25 | About 0.25 | About 0.25 |
| Hypromellose E3 2910 | — | About 0.20 | — | About 0.20 |
| Hypromellose E4M 2910 | — | — | About 0.36 | — |
| Boric Acid | About 0.52 | About 0.52 | About 0.52 | About 0.52 |
| Sodium Borate | About 0.06 | About 0.06 | About 0.06 | About 0.06 |
| Disodium Phosphate | About 0.027 | About 0.027 | About 0.027 | About 0.027 |
| Sodium Citrate Dihydrate | About 0.0009 | About 0.0009 | About 0.0009 | About 0.0009 |
| Potassium Chloride | About 0.18 | About 0.18 | About 0.18 | About 0.18 |
| Sodium Chloride | About 0.15 | About 0.12 | About 0.12 | About 0.12 |
| 50% Aqueous Solution of Sodium Lactate | About 0.057 | About 0.056 | About 0.056 | About 0.056 |
| Magnesium Chloride | About 0.013 | About 0.013 | About 0.013 | About 0.013 |
| Glucose | About 0.004 | About 0.004 | About 0.004 | About 0.004 |
| Glycine | About 0.00002 | About 0.00002 | About 0.00002 | About 0.00002 |
| Ascorbic Acid | About 0.00001 | About 0.00001 | About 0.00001 | About 0.00001 |
| Polyquaternium 42 | About 0.003 | About 0.003 | About 0.003 | About 0.003 |
| Purified Water | QS | QS | QS | QS |
| total | 100.00% | 100.00% | 100.00% | 100.00%. |

2. A composition, comprising a formulation selected from:

| INGREDIENT | A % w/w | B % w/w |
|---|---|---|
| Tetrahydrozoline Hydrochloride | 0.05 | 0.05 |
| Polyethylene Glycol 400 | 0.40 | — |
| Polysorbate 80 | — | 1.0 |
| Propylene Glycol | 0.30 | — |
| Sodium CMC | 0.6 | 0.6 |
| Boric Acid | 0.52 | 0.52 |
| Sodium Borate | 0.06 | 0.06 |
| Disodium Phosphate | 0.027 | 0.027 |
| Sodium Citrate | 0.0009 | 0.0009 |
| Potassium Chloride | 0.18 | 0.18 |
| Sodium Chloride | 0.10 | 0.26 |
| 50% Aqueous Solution of Sodium Lactate | 0.056 | 0.056 |
| Magnesium Chloride | 0.013 | 0.013 |
| Glucose | 0.004 | 0.004 |
| Glycine | 0.00002 | 0.00002 |
| Ascorbic Acid | 0.00001 | 0.00001 |
| Polyquaternium 42 | 0.003 | 0.003 |
| Purified Water | 97.69 | 97.30 |
| total | 100.00% | 100.00%. |

3. A composition, comprising a formulation selected from:

| INGREDIENT | A % w/w | B % w/w | C % w/w | D % w/w |
|---|---|---|---|---|
| Tetrahydrozoline Hydrochloride | 0.05 | — | — | — |
| Polyethylene Glycol 400 | — | 0.400 | — | — |
| Glycerin | 0.50 | 0.25 | — | — |
| Hypromellose E3 2910 | — | 0.20 | — | — |
| Boric Acid | 1.00 | 1.00 | 1.00 | 1.00 |
| Sodium Borate | 0.0045 | 0.0045 | 0.0045 | 0.0045 |
| Disodium Phosphate | — | — | 0.027 | — |
| Sodium Citrate Dihydrate | 0.0009 | 0.0009 | 0.0009 | 0.0009 |
| Potassium Chloride | — | — | 0.179 | — |
| Sodium Chloride | 0.140 | 0.140 | 0.12 | 0.12 |
| 50% Aqueous Solution of Sodium Lactate | 0.057 | 0.057 | 0.057 | 0.057 |
| Magnesium Chloride | — | — | 0.013 | — |
| Glucose | 0.040 | 0.40 | 0.036 | 0.036 |
| Glycine | 0.00002 | 0.00002 | 0.00002 | 0.0005 |
| Ascorbic Acid | 0.00001 | 0.00001 | 0.00001 | 0.00001 |
| Polyquaternium 42 | 0.003 | 0.003 | 0.003 | 0.003 |
| Purified Water | 98.206 | 97.544 | 98.56 | 98.778 |
| total | 100.00% | 100.00% | 100.00% | 100.00%. |

4. A composition, comprising a formulation selected from:

| INGREDIENT | A % w/w | B % w/w | C % w/w |
|---|---|---|---|
| Sodium Hyaluronate | 0.20 | — | 0.07 |
| Tamarind Seed Polysaccharide | — | 0.5 | 0.180 |
| Polyethylene Glycol 400 | 1 | 1 | 0.40 |
| Glycerin | 0.25 | 0.25 | 0.10 |
| Hypromellose E3 2910 | 0.20 | 0.20 | 0.07 |
| Boric Acid | 0.80 | 0.80 | 0.80 |
| Disodium Phosphate | 0.027 | 0.027 | 0.027 |
| Sodium Citrate Dihydrate | 0.28 | 0.25 | 0.18 |
| Potassium Chloride | 0.18 | 0.18 | 0.18 |

-continued

| INGREDIENT | A % w/w | B % w/w | C % w/w |
|---|---|---|---|
| 50% Aqueous Solution of Sodium Lactate | 0.057 | 0.057 | 0.057 |
| Magnesium Chloride | 0.013 | 0.013 | 0.013 |
| Glucose | 0.0036 | 0.0036 | 0.0036 |
| Glycine | 0.00002 | 0.00002 | 0.00002 |
| Ascorbic Acid | 0.00001 | 0.00001 | 0.00001 |
| Polyquaternium 42 | 0.003 | 0.003 | 0.003 |
| Purified Water | 96.986 | 96.716 | 97.916 |
| total | 100.00% | 100.00% | 100.00%. |

\* \* \* \* \*